(12) United States Patent
Cheung et al.

(10) Patent No.: US 11,913,072 B2
(45) Date of Patent: Feb. 27, 2024

(54) DETECTION OF MET EXON 14 DELETIONS AND ASSOCIATED THERAPIES

(71) Applicant: Roche Molecular Systems, Inc., Pleasanton, CA (US)

(72) Inventors: Cindy Cheung, Fremont, CA (US); Grantland Hillman, Oakland, CA (US); Xiaoju Max Ma, San Carlos, CA (US); Chitra Manohar, San Ramon, CA (US); Lily Wong, San Mateo, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 15/592,475

(22) Filed: May 11, 2017

(65) Prior Publication Data
US 2017/0327887 A1 Nov. 16, 2017

Related U.S. Application Data

(60) Provisional application No. 62/336,362, filed on May 13, 2016.

(51) Int. Cl.
| | | |
|---|---|---|
| *C12Q 1/68* | (2018.01) | |
| *C12Q 1/686* | (2018.01) | |
| *C12Q 1/6876* | (2018.01) | |
| *C12Q 1/6886* | (2018.01) | |

(52) U.S. Cl.
CPC .......... *C12Q 1/6876* (2013.01); *C12Q 1/686* (2013.01); *C12Q 1/6886* (2013.01); *C12Q 2600/106* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 2010/0021884 A1* | 1/2010 | Hessels | ............... | C12Q 1/6886 435/6.14 |
| 2011/0092375 A1* | 4/2011 | Zamore | ............. | C12N 15/1031 506/7 |
| 2013/0122484 A1* | 5/2013 | El-Attrache | ............. | C12Q 1/70 435/5 |

FOREIGN PATENT DOCUMENTS

WO    2006056766 A2    6/2006

OTHER PUBLICATIONS

Kong-Beltran et al; Cancer Research, vol. 66, pp. 283-289; Jan. 1, 2006.*
Frampton et al; Cancer Discovery, Aug. 2015; pp. 850-859.*
Genbank Accession No. NM_001127500, 2015, NLM, NCBI.*
Johnson et al. (2003) Science 302:2141.
Yan et al. (2013) J. Clin. Pathology 66:985.
Togashi et al. (2015) Lung Cancer 90:590.
Park et al. (2015) Lung Cancer 90:381.
Dodge et al. (2016) Association of Molecular Pathology Meeting Poster.
Lee et al. (2015) Oncotarget 6:28211.
Awad, M.M., et al., MET Exon 14Mutations in Non-Small-Cell Lung Cancer Are Associated With Advanced Age and Stage-Dependent MET Genomic Amplification and c-Met Overexpression, Journal of Clinical Oncology, 2016, pp. 721-730, vol. 34, No. 7.
Paweletz, C. P. et al., Bias-Corrected Targeted Next-Generation Sequencing for Rapid, Multiplexed Detection of Actionable Alterations in Cell-Free DNA from Advanced Lung Cancer Patients, Clinical Cancer Research, 2016, pp. 915-922, vol. 22, No. 4.
Summons to attend oral proceedings issued Oct. 14, 2022 in Application No. 17726561.8, 7 pages.
Wang, Z., et al., Quantification and Dynamic Monitoring of EGFR T790M in Plasma Cell-Free DNA by Digital PCR for Prognosis of EGFR-TKI Treatment in Advanced NSCLC, PLOS ONE, 2014, e110780, pp. 1-7, vol. 9, No. 11.

* cited by examiner

*Primary Examiner* — Jehanne S Sitton
(74) *Attorney, Agent, or Firm* — Daniel E. Agnew; David J. Chang

(57) ABSTRACT

Provided herein are methods and compositions to detect MET exon 14 skipping using RT-PCR, and methods of treating individuals with MET exon 14 deleted cancers.

9 Claims, 13 Drawing Sheets

Specification includes a Sequence Listing.

US 11,913,072 B2

DETECTION OF MET EXON 14 DELETIONS AND ASSOCIATED THERAPIES

CROSS-REFERENCE TO RELATED APPLICATIONS

The present application claims priority to U.S. Provisional Application No. 62/336,362 filed May 13, 2016, the disclosure of which is incorporated herein in its entirety.

SEQUENCE LISTING

The instant application contains a Sequence Listing which has been filed electronically in ASCII format and is hereby incorporated by reference in its entirety. Said ASCII copy, created on Apr. 28, 2017, is named 33633-US1_SL.txt and is 13,728 bytes in size.

BACKGROUND Of THE INVENTION

MET is a tyrosine kinase and proto-oncogene encoded on human chromosome 7. The preprotein is cleaved to form alpha and beta subunits which remain associated via disulfide bonds, and act as a receptor for Hepatocyte Growth Factor. Activated MET induces the PI3K-AKT-mTOR pathway, involved in cell survival, and the RAS-RAF-MEK-ERK pathway, involved in cell proliferation.

Mutations in MET are associated with a number of cancers, including renal, gastric, nervous system, sarcomas, and lung cancer. Mutations that result in higher activity or expression, or deletion of negative regulation sites are often implicated in these cancers. In particular, deletion of exon 14 and the negative regulation site at Tyr 1003 is associated with a significant percentage of non-small cell lung cancers (NSCLC) and adenocarcinomas. CBL, an E3 ubiquitin protein ligase, binds Tyr 1003 on the MET protein. MET is not degraded normally when the site is deleted. The resulting dysregulation of MET causes sustained activation of downstream cell proliferation and survival pathways. Detection of MET exon 14 deletion is more predictive of a positive therapeutic response to MET inhibitors than detection of gene amplification or increased mRNA or protein expression.

Mutations that cause MET exon 14 deletions are heterogeneous, often affecting splice acceptor or donor sites. Because of the heterogeneity, current detection methods are limited to next generation sequencing (NGS).

SUMMARY OF THE INVENTION

Provided herein are methods and compositions for detecting MET exon 14 deletions in human nucleic acid samples. In some embodiments, a method of detecting a MET exon 14 deletion comprises: (a) obtaining a nucleic acid sample from an individual (e.g., comprising RNA, DNA, or both RNA and DNA); (b) carrying out an amplification/detection reaction using the sample to selectively amplify and detect MET exon 13-exon 14 junction, MET exon 14-exon 15 junction, and MET exon 13-exon 15 junction; and (c) detecting the presence of a MET exon 14 deletion if the MET exon 13-exon junction 15 junction is detected. In some embodiments, the method further includes carrying out a reverse transcription reaction using the sample to produce cDNA before step (b). In some embodiments, the reverse transcription reaction and step (b) occur in a single vessel (tube, well, microfluidic chamber, etc.). In some embodiments, step (b) comprises contacting the cDNA with (i) a primer set and probe labeled with a first label that specifically amplify and detect MET exon 13-14 junction, (ii) a primer set and probe labeled with a second label that specifically amplify and detect MET exon 14-15 junction, and (iii) a primer set and probe labeled with a third label that specifically amplify and detect MET exon 13-15 junction. In some embodiments, step (c) comprises detection of the probe labeled with the third label.

In some embodiments, step (b) is a multiplex reaction, e.g., so that the primer sets and probes of (i), (ii) and (iii) are included in a single vessel. In some embodiments, the multiplex reaction further includes an internal control, e.g., primer set and probe labeled with a fourth label (e.g., labeled IC probe) that specifically amplify and detect an internal control. In some embodiments, step (b) is carried out in separate vessels, e.g., each carrying one of the primer sets and probes of (i), (ii), and (iv), optionally multiplexed with the internal control. In some embodiments, the reverse transcription and amplification/detection reactions are carried out using quantitative reverse transcription-PCR (qRT-PCR).

In some embodiments, the primer set for amplifying the MET exon 13-14 junction includes a forward primer having a sequence selected from the group consisting of: SEQ ID NOs:1-8 and a reverse primer having a sequence selected from the group consisting of SEQ ID NOs: 17-24. In some embodiments, the probe for detecting the MET exon 13-14 junction has a sequence selected from the group consisting of: SEQ ID NOs: 44-46. In some embodiments, the probe for detecting the MET exon 13-14 junction has the sequence of SEQ ID NO:44. In some embodiments, the probe for detecting the MET exon 13-14 junction has the sequence of SEQ ID NO:45. In some embodiments, the probe for detecting the MET exon 13-14 junction has the sequence of SEQ ID NO:46. In some embodiments, the primer set for amplifying the MET exon 14-15 junction includes a forward primer having a sequence selected from the group consisting of: SEQ ID NOs:9-16 and a reverse primer having a sequence selected from the group consisting of: SEQ ID NOs: 25-38. In some embodiments, the probe for detecting the MET 14-15 junction has a sequence selected from the group consisting of: SEQ ID NOs: 47-50. In some embodiments, the probe for detecting the MET 14-15 junction has the sequence of SEQ ID NO:47. In some embodiments, the probe for detecting the MET 14-15 junction has the sequence of SEQ ID NO:48. In some embodiments, the probe for detecting the MET 14-15 junction has the sequence of SEQ ID NO:49. In some embodiments, the probe for detecting the MET 14-15 junction has the sequence of SEQ ID NO:50. In some embodiments, the primer set for amplifying the MET exon 13-15 junction includes a forward primer selected from the group consisting of: SEQ ID NOs:1-8 and a reverse primer selected from the group consisting of: SEQ ID NOs: 25-38. In some embodiments, the probe for detecting the MET exon 13-15 junction has a sequence selected from the group consisting of SEQ ID NOs: 39-43 and 51-54. In some embodiments, the probe for detecting the MET 13-15 junction has the sequence of SEQ ID NO:39. In some embodiments, the probe for detecting the MET 13-15 junction has the sequence of SEQ ID NO:40. In some embodiments, the probe for detecting the MET 13-15 junction has the sequence of SEQ ID NO:41. In some embodiments, the probe for detecting the MET 13-15 junction has the sequence of SEQ ID NO:42. In some embodiments, the probe for detecting the MET 13-15 junction has the sequence of SEQ ID NO:43. In some embodiments, the probe for detecting the MET 13-15 junction has the sequence of SEQ ID NO:51. In some embodiments, the probe for detecting the MET 13-15 junction has the sequence of SEQ ID NO:52. In some embodiments, the probe for detecting the MET 13-15 junction has the sequence of SEQ ID NO:53. In some embodiments, the probe for detecting the MET 13-15 junction has the sequence of SEQ ID NO:54.

In some embodiments, a method of detecting a MET exon 14 deletion comprises: (a) obtaining a nucleic acid sample from an individual (e.g., comprising RNA, DNA, or both RNA and DNA); (b) carrying out an amplification/detection reaction using the sample to selectively amplify and detect a MET exon 13-exon 15 junction; and (c) detecting the presence of a MET exon 14 deletion if the MET exon 13-exon 15 junction is detected. In some embodiments, the method further includes carrying out a reverse transcription reaction suing the sample to produce cDNA before step (b). In some embodiments, the reverse transcription reaction and step (b) occur in a single vessel (tube, well, microfluidic chamber, etc.). In some embodiments, step (b) comprises contacting the cDNA with a primer set and labeled probe (e.g., with a non-naturally occurring fluorophore or fluorophore and quencher) that specifically amplify and detect MET exon 13-15 junction. In some embodiments, the primer et comprises a forward primer complementary to a sequence in MET exon 13 and a reverse primer complementary to a sequence in MET exon 15. In some embodiments, the labeled probe specifically hybridizes to the amplification product of the primer set, and includes sequence complementary to exon 13 only exon 15 only, or from both exon 13 and 15. In some embodiments, step (c) comprises detection of the labeled probe. In some embodiments, the method includes in step (b), carrying out an amplification/detection reaction using the sample to selectively amplify and detect an internal control, and in step (c), detecting the presence of the internal control if the internal control is detected. In some embodiments, amplification and detection of the internal control comprises contacting the cDNA with a primer set and labeled IC probe (e.g., with a non-naturally occurring fluorophore or fluorophore/quencher) that specifically amplify and detect the internal control. In some embodiments, step (c) comprises detection of the labeled IC probe.

In some embodiments, the primer set for amplifying the MET exon 13-15 junction includes a forward primer selected from the group consisting of: SEQ ID NOs:1-8 and a reverse primer selected from the group consisting of: SEQ ID NOs: 25-38. In some embodiments, the probe for detecting the MET exon 13-15 junction has a sequence selected from the group consisting of: SEQ ID NOs: 39-43 and 51-54. In some embodiments, the probe for detecting the MET exon 13-15 junction has a sequence selected from the group consisting of: SEQ ID NO: 43, SEQ ID NO:52, and SEQ ID NO:53. In some embodiments, the probe for detecting the MET 13-15 junction has the sequence of SEQ ID NO:39. In some embodiments, the probe for detecting the MET 13-15 junction has the sequence of SEQ ID NO:40. In some embodiments, the probe for detecting the MET 13-15 junction has the sequence of SEQ ID NO:41. In some embodiments, the probe for detecting the MET 13-15 junction has the sequence of SEQ ID NO:42. In some embodiments, the probe for detecting the MET 13-15 junction has the sequence of SEQ ID NO:43. In some embodiments, the probe for detecting the MET 13-15 junction has the sequence of SEQ ID NO:51. In some embodiments, the probe for detecting the MET 13-15 junction has the sequence of SEQ ID NO:53. In some embodiments, the probe for detecting the MET 13-15 junction has the sequence of SEQ ID NO:53. In some embodiments, the probe for detecting the MET 13-15 junction has the sequence of SEQ ID NO:54.

In some embodiments, step (b) is a multiplex reaction, e.g., so that the primer sets and probes are included in a single vessel. In some embodiments, the reverse transcription and amplification/detection reactions are carried out using quantitative reverse transcription-PCR (qRT-PCR).

In some embodiments, the sample is enriched for RNA before reverse transcription. In some embodiments, the sample is from a non-invasive source (e.g., blood, plasma, serum, urine, mucosal swab, saliva, skin, etc.). In some embodiments, the sample is a biopsy, e.g., a tumor biopsy, optionally an FFPET sample. In some embodiments, the individual has cancer, e.g., lung, renal, gastric, neuronal cancer, sarcoma, or adenocarcinoma. In some embodiments the individual has NSCLC.

In some embodiments, the method further comprises providing treatment for the individual with a MET inhibitor if a MET exon 14 deletion is detected. In some embodiments, the method further comprises providing treatment for the individual with an inhibitor of a downstream effector of MET (e.g., an inhibitor of the PI3K-AKT-mTOR or RAS-RAF-MEK-ERK pathway), or with standard chemotherapy, if a MET exon 14 deletion is detected.

Further provided are methods of providing a treatment for an individual comprising: (a) obtaining a nucleic acid sample from an individual (e.g., comprising RNA both RNA and DNA); (b) carrying out an amplification/detection reaction using the sample to selectively amplify and detect MET exon 13-exon 14 junction, MET exon 14-exon 15 junction, and MET exon 13-exon 15 junction; (c) detecting the presence of a MET exon 14 deletion if the MET exon 13-exon 15 junction is detected; and (d) providing treatment for the individual with a MET inhibitor if a MET exon 14 deletion is present. In some embodiments, the method further includes carrying out a reverse transcription reaction using the sample to produce cDNA before step (b). In some embodiments, the reverse transcription reaction and step (b) occur in a single vessel (tube, well, microfluidic chamber, etc.). In some embodiments, step (b) comprises contacting the cDNA with (i) a primer set and probe labeled with a first label that specifically amplify and detect MET exon 13-14 junction, (ii) a primer set and probe labeled with a second label that specifically amplify and detect MET exon 14-15 junction, and (iii) a primer set and probe labeled with a third label that specifically amplify and detect MET exon 13-15 junction. In some embodiments, step (c) comprises detection of the probe labeled with the third label.

In some embodiments, step (b) is a multiplex reaction, e.g., so that the primer sets and probes of (i), (ii) and (iii) are included in a single vessel. In some embodiments, the multiplex reaction further includes an internal control, e.g., a primer set and probe labeled with a fourth label (e.g., labeled IC probe) that specifically amplify and detect an internal control. In some embodiments, step (b) is carried out in separate vessels, e.g., each carrying one of the primer sets and probes of (i), (ii), and (iv), optionally multiplexed with the internal control. In some embodiments, the reverse transcription and amplification/detection reactions are carried out using quantitative reverse transcription-PCR (qRT-PCR).

In some embodiments, the method of providing a treatment for an individual comprises: (a) obtaining a nucleic acid sample from an individual (e.g., comprising RNA, DNA, or both RNA and DNA); (b) carrying out an amplification/detection reaction using the sample to selectively amplify and detect MET exon 13-exon 15 junction; (c) detecting the presence of a MET exon 14 deletion if the MET exon 13-exon 15 junction is detected; and (d) providing treatment for the individual with a MET inhibitor if a MET exon 14 deletion is present. In some embodiments, the method further includes carrying out a reverse transcription reaction using the sample to produce cDNA before step (b). In some embodiments, the reverse transcription reaction and step (b) occur in a single vessel (tube, well, microfluidic chamber, etc.). In some embodiments, step (b) comprises contacting the cDNA with a primer set and labeled probe that specifically amplify and detect MET exon 13-15 junction. In some embodiments, the primer set comprises a forward primer complementary to a sequence in MET exon 13 and a revere primer complementary to a sequence in MET exon 15. In some embodiments, the labeled probe specifically hybridizes to the amplification product of the primer set, and includes sequence complementary to exon 13 only, exon 15 only, or from both exon 13 and 15. In some embodiments, step (c) comprises detection of the labeled probe. In some embodiments, the method includes in step (b), carrying out an amplification/detection reaction using the sample to selectively amplify and detect an internal control, and in step (c), detecting the presence of the internal control if the internal control is detected. In some embodiments, amplification and detection of the internal control comprises contacting the cDNA with a primer set and labeled IC probe (e.g., with a non-naturally occurring fluorophore or fluorophore and quencher) that specifically amplify and detect the internal control. In some embodiments, step (c) comprises detection of the labeled IC probe.

In some embodiments, step (b) is a multiplex reaction, e.g., so that the primer sets and probes are included in a single vessel. In some embodiments, the reverse transcription and amplification/detection reactions are carried out using quantitative reverse transcription-PCR (qRT-PCR).

In some embodiments, the sample is enriched for RNA before reverse transcription. In some embodiments, the sample is from a non-invasive source (e.g., blood, plasma, serum, urine, mucosal swab, saliva, skin, etc.). In some embodiments, the sample is a biopsy, e.g., a tumor biopsy, optionally an FFPET sample. In some embodiments, the individual has cancer, e.g., lung, renal, gastric, neuronal cancer, sarcoma, or adenocarcinoma. In some embodiments the individual has NSCLC.

In some embodiments, the method further comprises providing treatment for the individual with an inhibitor of a downstream effector of MET (e.g., an inhibitor of the PI3K-AKT-mTOR or RAS-RAF-MEK-ERK pathway), or with standard chemotherapy, if a MET exon 14 deletion is detected.

Further provided is a method of identifying an individual with cancer comprising: (a) obtaining a sample comprising RNA from the individual; (b) carrying out a reverse transcription reaction on the RNA to produce cDNA; (c) carrying out an amplification reaction comprising contacting cDNA with a primer set and labeled probe that specifically amplify and detect MET exon 13-15 junction (exon 13-15 primer set and labeled exon 13-15 probe); and (d) detecting the presence of a MET exon 14 deletion if an amplification product is formed and detected by the exon 13-15 primer set and labeled exon 13-15 probe; whereby the presence of a MET exon 14 deletion mutation in the individual's sample indicates sensitivity of said individual to a MET inhibitor compound. In some embodiments, the method further comprises identifying an individual indicating sensitivity to an inhibitor of a downstream effector of MET (e.g., an inhibitor of the PI3K-AKT-mTOR or RAS-RAF-MEK-ERK pathway), or with standard chemotherapy, if a MET exon 14 deletion is detected.

Further provided are methods of identifying an individual with cancer comprising: (a) obtaining a nucleic acid sample fro man individual (e.g., comprising RNA both RNA and DNA); (b) carrying out an amplification/detection reaction using the sample to selectively amplify and detect MET exon 13-exon 14 junction, MET exon 14-exon 15 junction, and MET exon 13-exon 15 junction; and (c) detecting the presence of a MET exon 14 deletion if the MET exon 13-exon 15 junction is detected; whereby the presence of a MET exon 14 deletion mutation in the individual's sample indicates sensitivity of said individual to a MET inhibitor compound. In some embodiments, the method further includes carrying out a reverse transcription reaction using the sample to produce cDNA before step (b). In some embodiments, the reverse transcription reaction and step (b) occur in a single vessel (tube, well, microfluidic chamber, etc.). In some embodiments, step (b) comprises contacting the cDNA with (i) a primer set and probe labeled with a first label that specifically amplify and detect MET exon 13-14 junction, (ii) a primer set and probe labeled with a second label that specifically amplify and detect MET exon 14-15 junction, and (iii) a primer set and probe labeled with a third label that specifically amplify and detect MET exon 13-15 junction. In some embodiments, step (c) comprises detection of the probe labeled with the third label. In some embodiments, step (b) is a multiplex reaction, e.g., so that the primer sets and probes of (i), (ii), and (iii) are included in a single vessel. In some embodiments, the multiplex reaction further includes an internal control, e.g., a primer set and probe labeled with a fourth label (e.g., labeled IC probe) that specifically amplify and detect an internal control. In some embodiments, step (b) is carried out in separate vessels, e.g., each carrying one of the primer sets and probes of (i), (ii), and (iv), optionally multiplexed with the internal control. In some embodiments, the reverse transcription and amplification/detection reactions are carried out using quantitative reverse transcription-PCR (qRT-PCR).

In some embodiments, the method of identifying an individual with cancer comprises: (a) obtaining a nucleic acid sample from an individual (e.g., comprising RNA, DNA, or both RNA and DNA); (b) carrying out an amplification/detection reaction using the sample to selectively amplify and detect MET exon 13-exon 15 junction; and (c) detecting the presence of a MET exon 14 deletion if the MET exon 13-exon 15 junction is detected; whereby the presence of a MET exon 14 deletion mutation in the individual'sample indicates sensitivity of said individual to a MET inhibitor compound. In some embodiments, the method further includes carrying out a reverse transcription reaction using the sample to produce cDNA before step (b). In some embodiments, the reverse transcription reaction and step (b) occur in a single vessel (tube, well, microfluidic chamber, etc.). In some embodiments, step (b) comprises contacting the cDNA with a primer set and labeled probe that specifically amplify and detect MET exon 13-15 junction. In some embodiments, the primer set comprises a forward primer complementary to a sequence in MET exon 13 and a reverse primer complementary to a sequence in MET exon 15. In some embodiments, the labeled probe specifically hybridizes to the amplification product of the primer set, and includes sequence complementary to exon 13 only, exon 15 only, or from both exon 13 and 15. In some embodiments, step (c) comprises detection of the labeled probe. In some embodiments, the method includes in step (b), carrying out an amplification/detection reaction using the sample to selectively amplify and detect an internal control, and in step (c), detecting the presence of the internal control if the internal control is detected. In some embodiments, amplifications and detection of the internal control comprises contacting the cDNA with a primer set and labeled IC probe (e.g., with a non-naturally occurring fluorophore or fluorophore and quencher) that specifically amplify and detect the internal control. In some embodiments, step (c) comprises detection of the labeled IC probe.

In some embodiments, step (b) is a multiplex reaction, e.g., so that the primer sets and probes are included in a single vessel. In some embodiments, the reverse transcription and amplification/detection reactions are carried out using quantitative revere transcription-PCR (qRT-PCR).

In some embodiments, the method further comprises identifying an individual with cancer, wherein, if a MET exon 14 deletion is detected in the individual's sample, the individual's sample indicates sensitivity of said individual to an inhibitor of a downstream effector of MET (e.g., an inhibitor of the PI3K-AKT-mTOR or RAS-RAF-MEK-ERK pathway), or with standard chemotherapy.

Further provided are kits, e.g., for detecting MET exon 14 deletion in a nucleic acid sample. In some embodiments, the kit comprises (a) a primer set and a probe labeled with a first label that specifically amplify and detect MET exon 13-14 junction; (b) a primer set and a probe labeled with a second label that specifically amplify and detect MET exon 14-15 junction; and a primer set and a probe labeled with a third label that specifically amplify and detect MET exon 13-15 junction. In some embodiments, the sequences of the primers and probes are set forth as described above herein. In some embodiments, the kit further comprises (d) a primer set and probe labeled with a fourth label that specifically amplify and detect an internal control. In some embodiments, the first, second, and third labels are the same (e.g., for detection in separate vessels). In some embodiments, the first and second labels are the same, but different than the third label. In some embodiments, the first, second, and third labels are different (e.g., for a multiple reaction).

In some embodiments, the kit comprises a primer set and a labeled probe (e.g., non-naturally labeled probe, e.g., with a fluorophore or fluorophore/quencher) that specifically amplify and detect MET exon 13-15 junction. In some embodiments, the primer set comprises a forward primer complementary to a sequence in MET exon 13 and a reverse primer complementary to a sequence in MET exon 15. In some embodiments, the labeled probe specifically hybridizes to the amplification product of the primer set, and includes sequence complementary to exon 13 only, exon 15 only, or from both exon 13 and 15. In some embodiments the sequences of the primers and probe are set forth as described above. In some embodiments, the kit further comprises (d) a primer set and labeled probe that specifically amplify and detect an internal control (e.g., labeled IC probe, distinctly from the labeled probe specific for the MET exon 13-15 junction amplification product).

In some embodiments, the kit further includes a reverse transcriptase enzyme and a thermostable DNA polymerase, or an enzyme that has both activities. In some embodiments, the kit further comprises buffer (e.g., buffer that facilitates amplification) and/or dNTPs. In some embodiments, the kit further comprises a positive control comprising nucleic acids encoding MET exon 14 deletion. In some embodiments, the kit further comprises a negative control comprising nucleic acids that do not encode MET exon 14 deletion.

In some embodiments, the kit further comprises components for purification (enrichment) of RNA from a sample from an individual.

DETAILED DESCRIPTION OF THE INVENTION

I. Introduction

Figure 1:
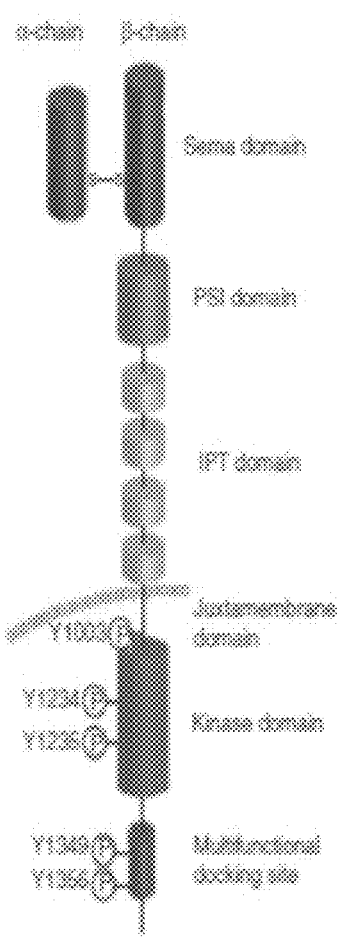
FIG. 1 depicts the alpha and beta subunits of mature MET, and shows the position of the ubiquination site a Y1003. CBL binds to Y1003 when it is phosphorylated (activated state) and targets MET for ubiquitin-mediated degradation. Y1003 is not present in exon 14 deleted MET.

Provided herein are novel quantitative reverse transcription (qRT)-PCR assays to detect MET exon 14 deletion, despite the variable nature of mutations that cause exon 14 deletion. The presently described assays thus rely on proven, widely adopted technology and provide accurate, reproducible, and rapid results. The results provided herein show that the assays can be effectively multiplexed and carried out in a single tube, while still providing extraordinarily specific and sensitive results.

II. Definitions

The term "multiplex" refers to an assay in which more than one target can be detected. For example, a multiplex reaction can include more than one primer set and more than one probe, specific for different portions or variants of a gene or transcript, or specific for different genes or transcripts.

The terms "receptacle," "vessel," "tube," "well," "chamber," "microchamber," etc. refer to a container than can hold reagents or an assay. If the receptacle is in a kit and holds reagents, or is being used for an amplification reaction, it can be closed or sealed to avoid contamination or evaporation. If the receptacle is being used for an assay, it can be open or accessible, at least during set up of the assay.

The terms "MET exon 14 deletion," "MET exon 14 skipping," and like terms refer to a MET gene that is chromosomally rearranged or mutated, or a MET transcript that is spliced to remove at least a portion of exon 14 of MET, i.e., the portion encoding negative regulation site Tyr 1003 in the juxtamembrane region of the MET protein. Various mutations at the DNA level can result in exon 14 skipping (see, e.g., Kong-Beltran et al. (2006) Cancer Res. 66; Dhanasekharan et al. (2014) Nature Communication 10:1038). In some embodiments, the presently described assays detect deletion of the entire exon 14 of MET, which encodes 47 amino acids.

The term "obtaining a sample from an individual" means that a biological sample from the individual is provided for testing. The obtaining can be directly from the individual, or from a third party that directly obtained the sample from the individual.

The term "providing treatment for an individual" means that the treatment is actually administered to the individual (e.g., an in-patient injection), or that it is made available to the individual, so that the individual or third party actually administers the treatment.

The term "formed and detected," in reference to an amplification product, indicates that the amplification product is formed and detected at a level that is higher than a base-line negative level. The base-line can be based on a negative control, e.g., set at the level of signal generated by a wild type sample in the case of amplifying and detecting a mutant sequence. the base-line can also be set slightly above the signal of the negative control (e.g., 1-5%) to allow for some variation in assay performance while avoiding false positive results for the mutant sequence. One of skill in the art of nucleic acid detection will understand the appropriate controls and variation levels for a given assay.

The terms "nucleic acid," "polynucleotide," and "oligonucleotide" refer to polymers of nucleotides (e.g., ribonucleotides or deoxyribo-nucleotides) and includes naturally-occurring (adenosine, guanidine, cytosine, uracil and thymidine), non-naturally occurring, and modified nucleic acids. The term is not limited by length (e.g., number of monomers) of the polymer. A nucleic acid may be single-stranded or double-stranded and will generally contain 5'-3' phosphodiester bonds, although in some cases, nucleotide analogs may have other linkages. Monomers are typically referred to as nucleotides. The term "non-natural nucleotide" or "modified nucleotide" refers to a nucleotide that contains a modified nitrogenous base, sugar or phosphate group, or that incorporates a non-natural moiety in its structure. Examples of non-natural nucleotides include dideoxynucleotides, biotinylated, aminated, deaminated, alkylated, benzylated and fluorophore-labeled nucleotides.

The term "primer" refers to a short nucleic acid (an oligonucleotide) that acts as a point of initiation of polynucleotide strand synthesis by a nucleic acid polymerase under suitable conditions. Polynucleotide synthesis and amplification reactions typically include an appropriate buffer, dNTPs and/or rNTPs, and one or more optional cofactors, and are carried out at a suitable temperature. A primer typically includes at least one target-hybridized region that is at least substantially complementary to the target sequence (e.g., having 0, 1, 2, or 3 mismatches). This region of its typically about 8 to about 40 nucleotides in length, e.g., 12-25 nucleotides. A "primer set" refers to a forward and reverse primer that are oriented in opposite directions relative to the target sequence, and that produce an amplification product in amplification conditions. The primer set can further include and additional forward or reverse primer, e.g., to carry out allele specific amplification. A primer set can also share a forward or reverse primer with another primer set, e.g., a common forward or reverse primer. The terms forward primer and reverse primer are arbitrarily assigned and do not indicate orientation in relation to coding sequence, etc., unless otherwise noted.

As used herein, "probe" means any molecule that is capable of selectively binding to a specifically intended target biomolecule, for example, a nucleic acid sequence of interest that hybridizes to the probes. The probe is detectably labeled with at least on e non-nucleotide moiety (i.e., non-naturally occurring moiety). In some embodiments, the probe is labeled with a fluorophore and quencher.

The term "specifically amplifies" indicates that a primer set amplifies a target sequence more than non-target sequence at a statistically significant level. The term "specifically detects" indicates that a probe will detect a target sequence more than non-target sequence at a statistically significant level. As will be understood in the art, specific amplification and detection can be determined using a negative control, e.g., a sample that includes the same nucleic acids as the test sample, but not the target sequence. For example, primers and probes that specifically amplify and detect a target sequence result in a CT that is readily distinguishable from background (non-target sequence), e.g., a Ct that is at least 2, 3, 4, 5, 5-10, 1020, or 10-30 cycles less than background.

The words "complementary" or "complementarity" refer to the ability of a nucleic acid in a polynucleotide to form a base pair with another nucleic acid in a second polynucleotide. For example, the sequence A-G-T (A-G-U for RNA) is complementary to the sequence T-C-A (U-C-A for RNA). Complementarity may be partial, in which only some of the nucleic acids match according to base pairing or complete, where all the nucleic acids match according to base pairing. A probe or primer is considered "specific for" a target sequence if it is at least partially complementary to the target sequence. Depending on the conditions, the degree of complementarity to the target sequence is typically higher for a shorter nucleic acid such as a primer (e.g., greater than 80%, 90%, 95%, or higher) than for a longer sequence.

The terms "identical" or "percent identity," in the context of two or more nucleic acids, or two or more polypeptides, refer to two or more sequences or subsequences that are the same or have a specified percentage of nucleotides, or amino acids, that are the same (e.g., about 60% identity, e.g., at least any of 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nib.gov/BLAST. Such sequences are then said to be "substantially identical." Percent identity is typically determined over optimally aligned sequences, so that the definition applies to sequences that have deletions and/or additions, as well as those that have substitutions. The algorithms commonly used in the art account for gaps and the like. Typically, identity exists over a region comprising an a sequence that is at least about 8-25 amino acids or nucleotides in length, or over a region that is 50-100 amino acids or nucleotides in length, or over the entire length of the reference sequence.

The term "kit" refers to any manufacture (e.g., a package or a container) including at least one reagent, such as a nucleic acid probe or probe pool or the like, for specifically amplifying, capturing, tagging/converting or detecting RNA or DNA as described herein.

The term "amplification conditions" refers to conditions in a nucleic acid amplification reaction (e.g., PCR amplification) that allows for hybridization and template-dependent extension of the primers. The "amplicon" or "amplification product" refers to a nucleic acid molecule that contains all or a fragment of the target nucleic acid sequence and that is formed as the product of in vitro amplification by any suitable amplification method. One of skill will understand that a forward and revere primer (primer pair) defines the borders of an amplification product. The term "generate an amplification product" when applied to primers, indicates that the primers, under appropriate conditions (e.g., in the presence of a nucleotide polymerase and NTPs), will produce the defined amplification product. Various PCR conditions are described in *PCR Strategies* (Innis et al., 1995, Academic Press, San Diego, CA) at Chapter 14; *PCR Protocols: A Guide to Methods and Applications* (Innis et al., Academic Press, N.Y., 1990)

The term "amplification product" refers to the product of an amplification reaction. The amplification product includes the primers used to initiate each round of polynucleotide synthesis. An "amplicon" is the sequence targeted for amplification, and the term can also be used to refer to amplification product. The 5' and 3' borders of the amplicon are defined by the forward and reverse primers.

The term "sample" or "biological sample" refers to any composition containing or presumed to contain nucleic acid. the term includes purified or separated components of cells, tissues, or blood, e.g., DNA, RNA, proteins, cell-free portions, or cell lysates. In the context of the presently disclosed assay, the sample is typically FFPET, e.g., from a tumor or metastatic lesion. The sample can also be from frozen or fresh tissue, or from a liquid sample, e.g., blood or a blood component (plasma or serum), urine, semen, saliva, sputum, mucous, semen, tear, lymph, cerebral spinal fluid, mouth/throat rinse, bronchial alveolar lavage, material washed from a swab, etc. Samples also may include constituents and components of in vitro cultures of cells obtained from an individual including cell lines. The ample can also be partially processed from a sample directly obtained from an individual, e.g., cell lysate or blood depleted of red blood cells.

A "control" sample or value refers to a value that serves as a reference, usually a known reference, for comparison to a test sample or test conditions. For example a test sample can be taken from a test condition, e.g., from an individual suspected of having cancer, and compared to samples from known conditions, e.g., from a cancer-free individual (negative control), or from an individual known to have cancer (positive control). A control can also represent an average value or a range gathered from a number of tests or results. A control can also be prepared for reaction conditions. For example, a control for the presence, quality, and/or quantity of nucleic acid (e.g., internal control) can include primers or probes that will detect a sequence known to be present in the sample (e.g., a housekeeping gene such as beta actin, beta globin, glyceraldehyde 3-phosphate dehydrogenase (GAPDH), ribosomal protein L37 and L38, PPIase, EIF3, eukaryotic translation elongation factor 2 (eEF2), DHFR, or succinate dehydrogenase). A known added polynucleotide, e.g., having a designated length and/or sequence, can also be added. An example of a negative control is one free of nucleic acids, or one including primers or probes specific for a sequence that would not be present in the sample, e.g., from a different species. One of skill will understand that the selection of controls will depend on the particular assay, e.g., so that the control is cell type and organism appropriate. One of skill in the art will recognize that controls can be designed or assessment of any number of parameters. For example, a control can be devised to compare therapeutic benefit based on pharmacological data (e.g., half-life) or therapeutic measures (e.g., comparison of benefits and/or side effects). Controls can be designed for in vitro applications. One of skill in the art will understand which controls are valuable in a given situation and be able to analyze data based on comparisons to control values. Controls are also valuable for determining the significance of data. For example, if values for a given parameter are widely variant in controls, variation in the samples will not be considered as significant.

The terms "label," "tag," "detectable moiety," and like terms refer to a composition detectable by spectroscopic, photochemical, biochemical, immunochemical, chemical, or other physical means. For example, useful labels include fluorescent dyes, luminescent agents, radioisotopes (e.g., $^{32}$P, $^{3}$H), electron-dense reagents, or an affinity-based moiety, e.g., a poly-A (interacts with poly-T) or poly-T tag (interacts with poly-A), a His tag (interacts with Ni), or a strepavidin tag (separable with biotin). As used herein, a biomolecule (DNA, RNA, protein, etc.) attached to a label, tag, or detectable moiety is not a composition that occurs in nature.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et. al., MOLECULAR CLONING, A LABORATORY MANUAL, Cold Springs Harbor Press (Cold Springs Harbor, N.Y. 1989). The term "a" or "an" is intended to mean "one or more." The terms "comprise," "comprises," and "comprising," when preceding the recitation of a step or an element, are intended to mean that the addition of further steps or elements is optional and not excluded.

III. Nucleic Acid Samples

Samples for nucleic acid amplifications can be obtained from any source suspected of containing nucleic acid. In the context of the present disclosure, the ample is from a human source. In some embodiments, the sample is obtained in a non-invasive manner, e.g., blood or a blood fraction, urine, skin, swab, or saliva. Samples can also be taken from formalin fixed paraffin embedded tissue (FFPET), tissue biopsy, brochoalveolar lavage, or cultured cells (e.g., obtained from a patient, or representing a control). In some embodiments, the sample is taken from lung tissue or a cell population that includes lung cells, e.g., lung cancer cells.

In a sample that includes cells, the cells can be separated out (e.g., using size-based filtration or centrifugation), thereby leaving cell free nucleic acids (cfNA), including nucleic acids in exosomes, microvesicles, viral particles, or those circulating freely. Alternatively, the cells can be lysed to obtain cellular nucleic acids, either in the presence of magnetic glass particles (MGPs) or before addition of the cellular lysate to the MGPs.

In some embodiments, the nucleic acids (DNA, RNA, or both) are isolated from other components of the sample, e.g., proteins, membranes, lipids, etc., before amplification and/or detection. The terms "isolated," "separated," "purified," etc. do not indicate that the nucleic acids are 100% free of other substances, but that the nucleic acids are substantially enriched compared to the original sample. For example, purified nucleic acids can be 2-, 3-, 4-, 5-, 10-, 20-, 50-, 100-fold enriched compared to the original sample, or more. In some embodiments, purified nucleic acids are in aqueous solution having less than 20%, 10%, 5%, 2%, 1%, 0.5% or 0.1% non-nucleic acid residual from the sample.

In some embodiments, the presently described assays rely on mRNA encoding MET. Because many of the mutations causing exon 14 deletion are somatic, the deletion would be expected to occur in transcripts from any cell type expressing MET, e.g., epithelial cells. Samples can be taken from any cell or cell-free source suspected of carrying tumor nucleic acids (e.g., cancer biopsy or circulating nucleic acids).

Methods for isolating nucleic acids from biological samples are known, e.g., as described in Sambrook supra, and several kits are commercially available (e.g., Cobas® cfRNA Sample Preparation Kit, High Pure RNA Isolation Kit, High Pure Viral Nucleic Acid Kit, and MagNA Pure LC Total Nucleic Acid Isolation Kit, DNA Isolation Kit for Cells and Tissues, DNA Isolation Kit for Mammalian Blood, High Pure FFPET DNA Isolation Kit, available from Roche). In the context of the presently disclosed methods, RNA is collected though in some embodiments, the test can be used on previously prepared cDNA.

IV. Amplification and Detection

The nucleic acid sample (isolated or not) can be used for detection and quantification, e.g., using nucleic acid amplification, e.g., using any primer-dependent method. In some embodiments, a preliminary reverse transcription step is carried out (also referred to as RT-PCR, not to be confused with real time PCR). See, e.g., Hierro et al. (2006) 72:7148. The term "qRT-PCR" as used herein refers to reverse transcription followed by quantitative PCR. Both reactions can be carried out in a single tube without interruption, e.g., to add reagents. For example, a polyT primer can be used to reverse transcribe all mRNAs in a sample with a polyA tail, random oligonucleotides can be used, or a primer can be designed that is specific for a particular target transcript that will be reverse transcribed into cDNA. The cDNA can form the initial template strand to be for quantitative amplification (real time or quantitative PCR, i.e., RTPCR or qPCR). qPCR allows for reliable detection and measurement of products generated during each cycle of PCR process. Such techniques are well known in the art, and kits and reagents are commercially available, e.g., from Roche Molecular Systems, Life Technologies, Bio-Rad, etc. See, e.g., Pfaffl (2010) Methods: The ongoing evolution of qPCR vol. 50.

A separate reverse transcriptase and thermostable DNA polymerase can be used, e.g., in a two-step (reverse transcription followed by addition of DNA polymerase and amplification) or combined reaction (with both enzymes added at once). In some embodiments, the target nucleic acid is amplified with a thermostable polymerase with both reverse transcriptase activity and DNA template-dependent activity. Exemplary enzymes include Tth DNA polymerase, the C Therm Polymerase system, and those disclosed in US20140170730 and US20140051126. In some embodiments, Taq or a Taq derivative is used for amplification (e.g., Z05, C21, etc.). In some embodiments, the reverse transcriptase is from MMLV, AMV, or is a derivative thereof.

Probes for use as described herein can be labeled with a fluorophore and quencher (e.g., TaqMan, LightCycler, Molecular Beacon, Scorpion, or Dual Labeled probes). Appropriate fluorophores include FAM, JOE, JA270, TET, Cal Fluor Gold 540, HEX, VIC, Cal Fluor Orang 560, TAMRA, Cyanine 3, Quasar 570, Cal Fluor Red 590, Rox, Texas Red, Cyanine 5, Quasar 670, and Cyanine 5.5. Appropriate quenchers include TAMRA (for FAM, JOE, and TET), DABCYL, and BHQ1-3.

Detection devices are known in the art and can be selected as appropriate for the selected labels. Detection devices appropriate for quantitative PCR include the Cobas® and Light Cycler® systems (Roche), PRISM 7000 and 7300 real-time PCR systems (Applied Biosystems), etc. Six-channel detection is available on the CFX96 Real Time PCR Detection System (Bio-Rad) and Rotorgene Q (Qiagen), allowing for a higher degree of multiplexing.

Results can be expressed in terms of a threshold cycle (abbreviated as Ct, and in some instances Cq or Cp). A lower Ct value reflects the rapid achievement of a predetermined threshold level, e.g., because of higher target nucleic acid concentration or a more efficient amplification. A higher Ct value may reflect lower target nucleic acid concentration, or inefficient or inhibited amplification. The threshold cycle is generally selected to be in the linear range of amplification for a given target. In some embodiments, the Ct is set as the cycle at which the growth signal exceeds a pre-defined threshold line, e.g., in relation to the baseline, or by determining the maximum of the second derivation of the growth curve. Determination of Ct is known in the art, and described, e.g., in U.S. Pat. No. 7,363,168.

V. Kits

Provided herein are kits for multiplex qRT-PCR assays to detect MET exon 14 deletions in a sample. In some embodiments, the kit includes primer and probes for amplification, detection, and/or quantification of transcripts encoding MET exon 13-exon 14, exon 14-exon 15, and 13-exon 15 junctions.

The junction-specific primer sets and probes can be mixed and matched in any combination. In a detection system having 4 channels, each of the three junctions can be detected in a single vessel, along with an internal control. Alternatively, the assay can be carried out with a lower degree of multiplexing, or in non-multiplex fashion. For example, each junction can be individually detected in a separate vessel, e.g., with an internal control.

In some embodiments, the kit includes primers and a probe for amplification, detection and/or quantification of transcripts encoding MET exon 13-exon 15 junctions. These primers (e.g., RT primer, and forward and reverse primers that specifically amplify a MET exon 13-exon 15 junction amplification product) and probe (specific for the MET exon 13-exon 15 junction amplification product) can be mixed with primers and a probe that specifically amplify and detect an internal control, or provided in a separate vessel.

In some embodiments, the mixtures further comprise buffers, dNTPs, and other elements (e.g., cofactors or aptamers) appropriate for reverse transcription and amplification. Typically, the mixture is concentrated, so that an aliquot is added to the final reaction volume, along with sample (e.g., RNA), enzymes, and/or water. In some embodiments, the kit further comprises reverse transcriptase (or an enzyme with reverse transcriptase activity), and/or DNA polymerase (e.g., thermostable DNA polymerase such as Taq, ZO5, and derivatives thereof).

In some embodiments, the kit further includes components for RNA purification from a sample, e.g., a plasma or FFPET sample. For example, the kit can include components from the Cobas® 6800/8800 Sample Prep Kits, High Pure of MagNA Pure RNA Isolation Kits (Roche), miRNeasy or RNeasy FFPE Kits (Qiagen), PureLink FFPE RNA Isolation Kit (Thermo Fisher), ThruPLEX Plasma-seq (Beckman Coulter), etc.

In some embodiments, the kit further includes at least one control sample, e.g., nucleic acids from non-cancer sample (or pooled samples), or from a known MET exon 14 deleted sample (or pooled samples). In some embodiments, the kit further includes consumables, e.g., plates or tubes for nucleic acid preparation, tubes for sample collection, etc. In some embodiments, the kit further includes instructions for use, reference to a website, or software.

VI. MET-Associated Cancers and Therapies

MET mutations are associated with a number of different cancers, including renal, gastric, and those of the central nervous system, as well as sarcomas. MET exon 14 deletion in particular is associated with non-small cell lung cancer (NSCLC) and lung adenocarcinomas, found in 2% and 4% of these cancers, respectively. The 2016 National Comprehensive Cancer Network (NCCN) Guidelines now include MET exon 14 deletion in category 2A for emerging targeted agents for lung cancer patients with genetic alterations.

MET inhibitors crizotinib (also inhibits ALK and ROS1) and cabozantinib (also inhibits VEGFR2 and RET) have been shown to be effective for lung adenocarcinoma patients harboring MET exon 14 skipping. Additional small molecule MET inhibitors are being tested, including INCB28060 (Incyte), AMG-458 (Amgen), PF-04217903 (Pfizer), PF-02341066 (Pfizer), E7050 (Eisai), MK-2461 (Merck), BMS-777607 (BMS), JNJ-38877605 (Johnson & Johnson), ARQ197 (ArQule), GSK/1363089/XL880 (GSK/Exelexis), and XL184 (BMS/Exelexis). Additional MET inhibitors include biologics, e.g., antibodies or antibody fragments specific for MET (e.g., activated MET).

Patients having a MET exon 14 deletion can also benefit from standard chemotherapy. This can include CHOP (cyclophosphamide; doxorubicin; doxorubicin; vincristine; and prednisolone) or R-CHOP, which further includes rituximab and/or etoposide. The cocktail can be administered periodically for a set period of time, or until reduction in tumor size and/or symptoms are detected. For example, the CHOP or R-CHOP can be administered every 2 or 3 weeks. Treatment typically begins with a low dose so that side effects can be determined, and the dose increased until side effects appear or within the patient's tolerance.

VII. Examples

Figure 2:
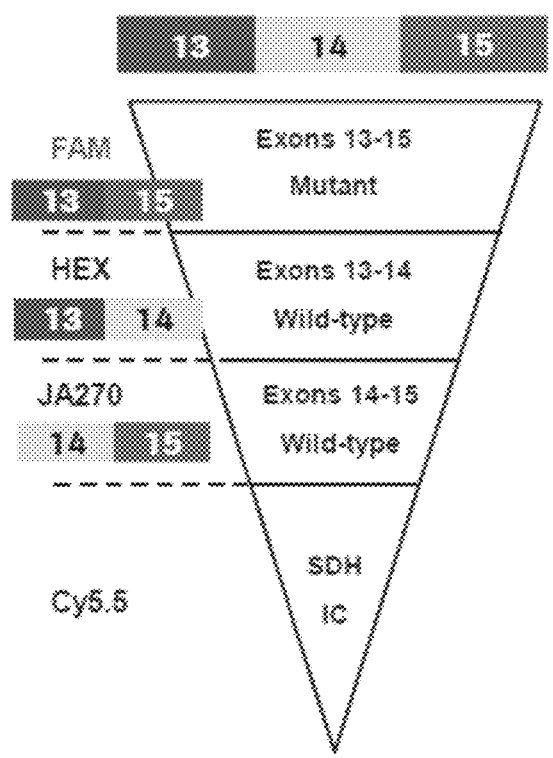
FIG. 2 shows an exemplary assay design for detection of MET exon 14 deletion. The mutant form is detected using a FAM-labeled probe specific for the exon 13-exon 15 junction, while the wild type forms are detected using a HEX-labeled probe specific for the exon 13-exon 14 junction and a JA270-labeled probe specific for the exon 14-exon 15 junction. An internal control is detected with a Cy5.5-labeled probe, e.g., to standardize for nucleic acid concentration and quality.
Figure 3:
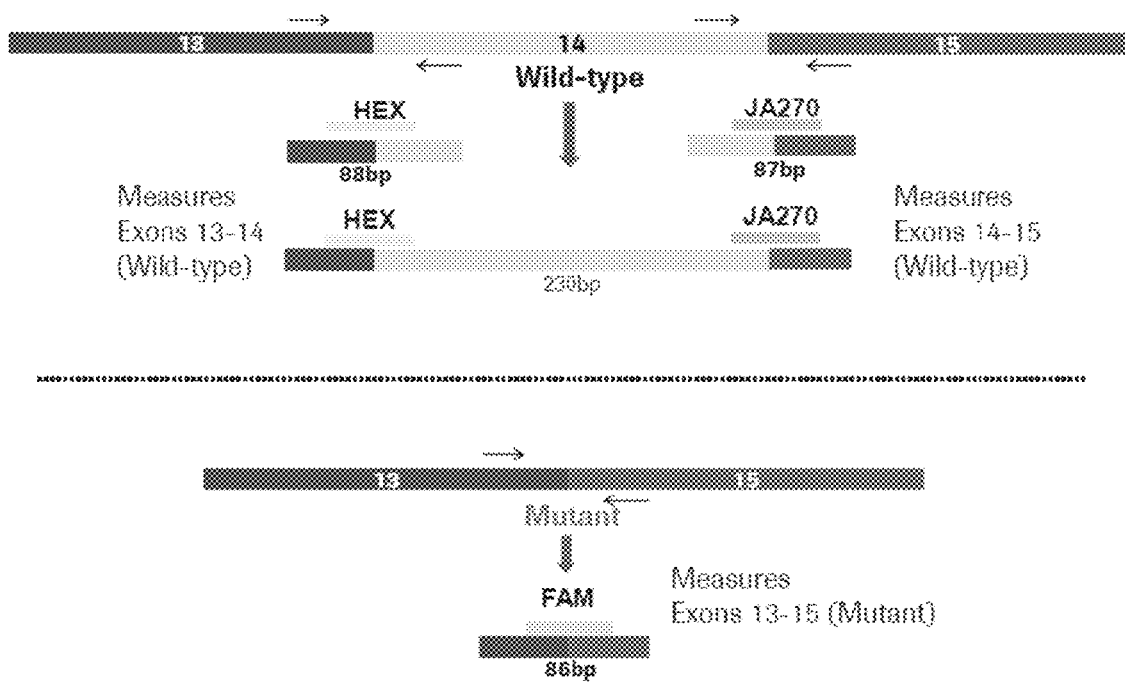
FIG. 3 provides further information about the exemplary assay design. Exons 13, 14, and 15 of wild type MET transcript are shown on top of the top panel. Primers are represented by arrows, and amplicons produced by the primers are shown just below hybridized to specific, labeled probes. The bottom panel shows exons 13 and 15 joined, exemplary primer positions, and the resulting amplicon hybridized to specific labeled probe.

A. Assay Design (FIGS. 2 and 3)

Primers were designed to amplify across the junction of exon 13-exon 15 (mutant or exon 14 deleted) and exon 13-exon 14 and exon 14-exon 15 (wild type). Probes specific for the junction point of each amplicon were also prepared, and labeled with different labels for multiplex amplification and detection. Primers and a probe were also designed for an internal control, in this case SDH (succinyl dehydrogenase).

Non-natural nucleic acids and mismatches from the target sequence were introduced to stabilize the specific target-oligo hybridizations. The best modifications and positions for mismatch are unpredictable. Suitable oligonucleotide sequences are shown in Table 1 below. MET13-FWD refers to a forward primer in MET exon 13; MET14-FWD refers to a forward primer in MET exon 14; MET14-REV refers to a reverse primer in MET exon 14; MET15-REV refers to a reverse primer in MET exon 15; MET13-15-PRB refers to a probe that hybridizes with nucleotides at the junction of MET exons 13 and 15; MET13-14-PRB refers to a probe that hybridizes with nucleotides at the junction of MET exons 13-14; and MET 14-15-PRB refers to a probe that hybridizes with nucleotides at the junction of MET exons 14-15; MET13-15-PRB9 is an antisense orientation probe that does not hybridize to MET exon 13-exon 15 amplification products, and that can be used for a control.

TABLE 1

| Primer Name | SEQ ID NO | Sequence |
|---|---|---|
| MET13-FWD1 | 1 | TTGGGTTTTCCTGTGGCT |
| MET13-FWD2 | 2 | TTGGGTTTTCCTGTGG<pdC>T |
| MET13-FWD3 | 3 | TTGGGTTTTCCTGTGGC<pdU> |
| MET13-FWD4 | 4 | TTGGGTTTTCCTGTGG<pdC><pdU> |
| MET13-FWD5 | 5 | CTTGGGTTTTCCTGTGGCT |
| MET13-FWD6 | 6 | CTTGGGTTTTCCTGTGGCTG |
| MET13-FWD7 | 7 | TGGGTTTTCCTGTGGCT |
| MET13-FWD8 | 8 | TTGGGTTTTCCTGTGGCTG |
| MET14-FWD1 | 9 | TCAAATGAATCTGTAGACTACCG |
| MET14-FWD2 | 10 | TCAAATGAATCTGTAGACTAC<pdC>G |
| MET14-FWD3 | 11 | TCAAATGAATCTGTAGACTA<pdC>CG |
| MET14-FWD4 | 12 | TCAAATGAATCTGTAGACTAC<5_Me_dC>G |
| MET14-FWD5 | 13 | AATGGTTTCAAATGAATCTGTAGACT |
| MET14-FWD6 | 14 | AAATGGTTTCAAATGAATCTGTAGACT |
| MET14-FWD7 | 15 | AGAAATGGTTTCAAATGAATCTGTAGA |
| MET14-FWD8 | 16 | GAAATGGTTTCAAATGAATCTGTAGAC |
| MET14-REV1 | 17 | GAGTGTGTACTCTTGCATCGTA |
| MET14-REV2 | 18 | GAGTGTGTACTCTTGCATCG<pdU>A |
| MET14-REV3 | 19 | GAGTGTGTACTCTTGCAT<G_Clamp>GT<N6_Bz_dA> |
| MET14-REV4 | 20 | GAGTGTGTACTCTTGCATCG<pdU><N6_Bz_dA> |
| MET14-REV5 | 21 | AGTGTGTACTCTTGCATCGT |
| MET14-REV6 | 22 | GAGTGTGTACTCTTGCATCGTA |
| MET14-REV7 | 23 | TGAGGAGTGTGTACTCTTGCA |
| MET14-REV8 | 24 | GAGGAGTGTGTACTCTTGCA |
| MET15-REV1 | 25 | TGCACTTGTCGGCATGAA |
| MET15-REV2 | 26 | CTGCACTTGTCGGCCATGAA |
| MET15-REV3 | 27 | CTGCACTTGTCGGCA<pdU>GAA |
| MET15-REV4 | 28 | CTGCACTTGTCGGCA<pdU>GA<N6_Bz_dA> |
| MET15-REV5 | 29 | CTTGTCGGCATGAACCGTT |
| MET15-REV6 | 30 | TTGTCGGCATGAACCGTT |
| MET15-REV7 | 31 | CTTGTCGGCATGAACCGT |
| MET15-REV8 | 32 | ACTTGTCGGCATGAACCGT |
| MET15-REV9 | 33 | TGCACTTGTCGGCATGAAC |
| MET15-REV10 | 34 | CTGCACTTGTCGGCATGAA |
| MET15-REV11 | 35 | GCACTTGTCGGCATGAACC |

TABLE 1-continued

| | SEQ ID NO | Sequence |
|---|---|---|
| MET15-REV12 | 36 | CTGCACTTGTCGGCATGAAC |
| MET15-REV13 | 37 | TTGTCGGCATGAACCGTTCT |
| MET15-REV14 | 38 | GTCGGCATGAACCGTTCT |

| Probe Name | SEQ ID NO | Sequence |
|---|---|---|
| MET13-15-PRB1 | 39 | \<FAM_Thr>AGAAAGC\<BHQ_2>AAATTAAAGATCAGTTTCCTAATTCAT |
| MET13-15-PRB2 | 40 | \<FAM_Thr>AGAAAGC\<BHQ_2>AAATTAAAGA\<pdU>\<pdC>AGTTTCCTAATTCAT |
| MET13-15-PRB3 | 41 | \<FAM_Thr>AGAAAGC\<BHQ_2>AAATTAAAGA\<pdU>\<5_Me_dC>AGTTTCCTAATTCAT |
| MET13-15-PRB4 | 42 | \<FAM_Thr>AGAAAGC\<BHQ_2>AAATTAAAGAT\<G_clamp>AGTTTCCTAATTCAT |
| MET13-15-PRB5 | 43 | \<FAM_Thr>AGAAAGC\<BHQ_2>AAATTAAAGA\<pdU>\<G_clamp>AGTTTCCTAATTCAT |
| MET13-14-PRB1 | 44 | \<HEX_Thr>AGAAAGCA\<BHQ_2>AATTAAAGATCTGGGCAGTGAATTAG |
| MET13-14-PRB2 | 45 | \<HEX_Thr>AGAAAGCA\<BHQ_2>AATTAAAGA\<pdU>\<pdC>TGGGCAGTGAATTAG |
| MET13-14-PRB3 | 46 | \<HEX_Thr>AGAAAGCA\<BHQ_2>AATTAAAGAT\<G_clamp>TGGGCAGTGAATTAG |
| MET14-15-PRB1 | 47 | \<JA270_Thr>AGCTACTTTT\<BHQ_2>CCAGAAGATCAGTTTCCTAATTCAT |
| MET14-15-PRB2 | 48 | \<JA270_Thr>AGCTACTTTT\<BHQ_2>CCAGAAGATCAGTTTCCTAATTC\<N6_Bz_dA>T |
| MET14-15-PRB3 | 49 | \<JA270_Thr>AGCTACTTTT\<BHQ_2>CCAGAAGAT\<G_clamp>AGTTTCCTAATTCAT |
| MET14-15-PRB4 | 50 | \<JA270_Thr>AGCTACTTTT\<BHQ_2>CCAGAAGA\<pdU>\<pdC>AGTTTCCTAATTCAT |
| MET14-15-PRB6 | 51 | \<FAM_Thr>AGAAA\<BHQ_2>GCAAATTAAAGA\<pdU>\<G_clamp>AGTTTCCTAATTCAT |
| MET13-15-PRB7 | 52 | \<FAM_Thr>AGAAA\<BHQ_2>ATTAAAGAT\<G_Clamp>AGTTTCCTAATTCATCTCAG |
| MET13-15-PRB8 | 53 | \<FAM_Thr>AGAAA\<BHQ_2>GATCAGTTTCCTAATTCATCTCAGAACGG |
| MET13-15-PRB9 | 54 | \<FAM_Thr>T\<pdU>AAA\<BHQ_2>GAT\<G_Clamp>AGTTTCCTAATTCATCTCAGAACGG |
| MET13-15-PRB10 Antisense control | 55 | \<FAM_Thr>AATTT\<BHQ_2>CTAGTCAAAGGATTAAGTAGAGTCTTGCC | pdU = C-5 propynyl-dU (non-natural substitute for T)
pdC = C-5 propynyl-dC (non-natural substitute for C)
5 MedC = 5-methyl-2'-dC(non-natural subsitute for C)
G clamp = AP-dC (non-natural substitute for C)
N6 Bz dA = N6-benzoyl-2'-deoxyadenosine (non-natural substitute for A)
FAM, HEX, JA270 = fluorophores
BHQ 2 = quencher

B. MET Exon 14 Multiplex Reaction with Cell Line Nucleic Acids

A multiplex assay was run with MET 13 FWD, MET 14 FWD, MET 14 REV, and MET 15 REV primers, and one each of the differently labeled MET13-14-PRB, MET13-15-PRB, and MET14-15-PRB probes. Internal control primer and Cy5.5-labeled probe were also included.

Figure 4:
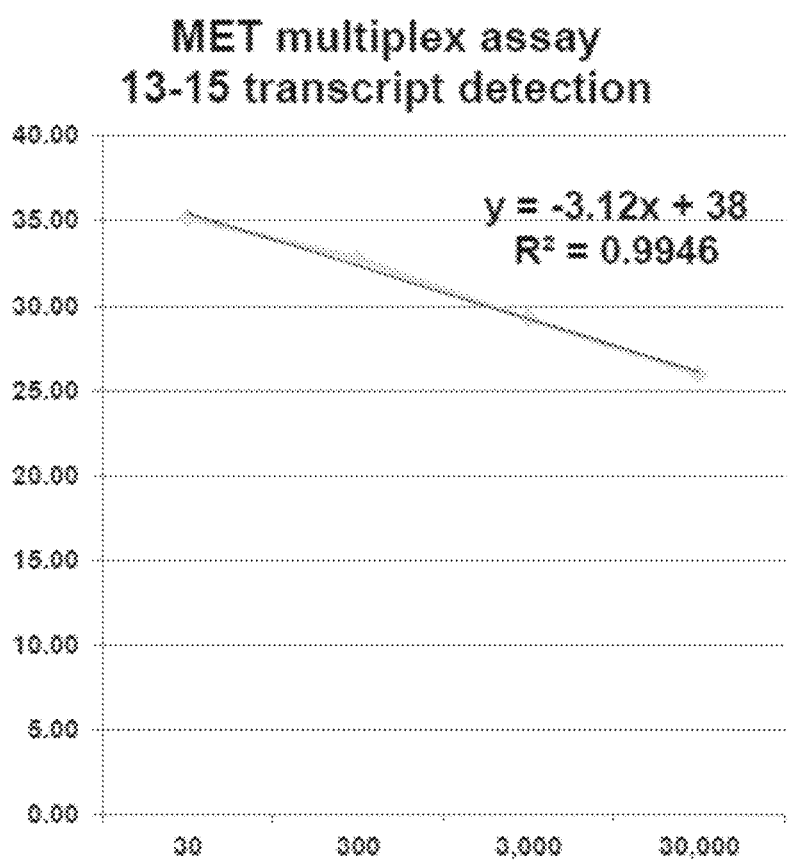
FIG. 4 shows the result of the multiplex reaction depicted in FIGS. 2 and 3 for the mutant form (FAM channel). The x-axis shows copy number of the mutant sequence and the y-axis shows Ct. The figure shows that Ct decreases with increasing copy number in a linear fashion, and that the assay is sensitive enough to detect 30 copies.
Figure 5:
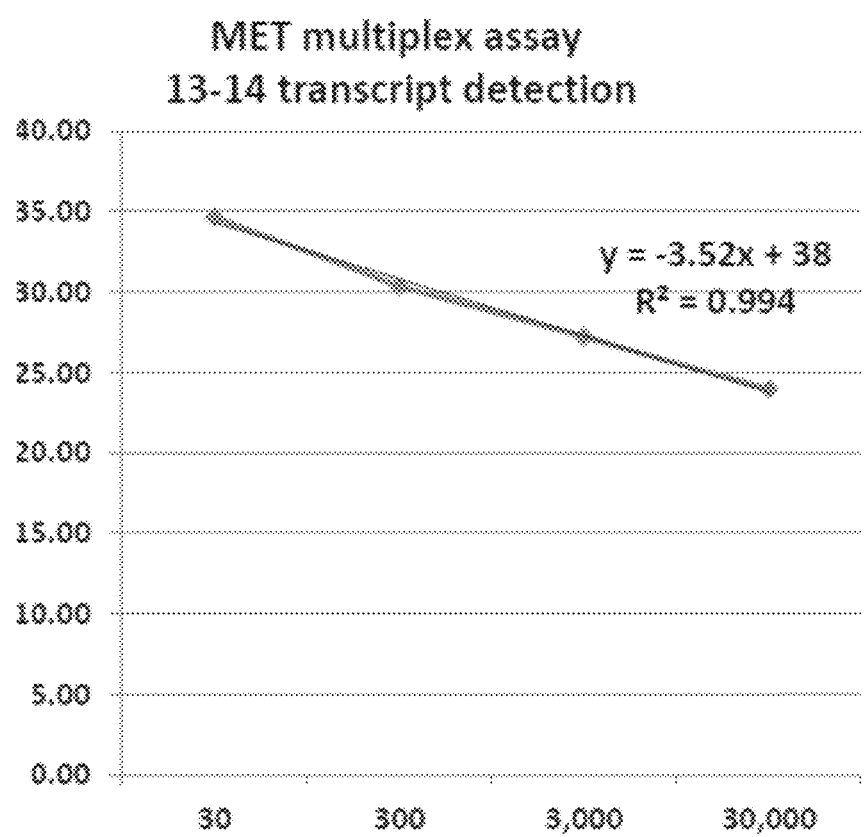
FIG. 5 shows the result of the multiplex reaction for the wild type form exon 13-exon 14 junction (HEX channel). As with the mutant reaction, Ct is inversely related to wild type copy number, the reaction is linear, and sensitive enough to detect 30 copies.
Figure 6:
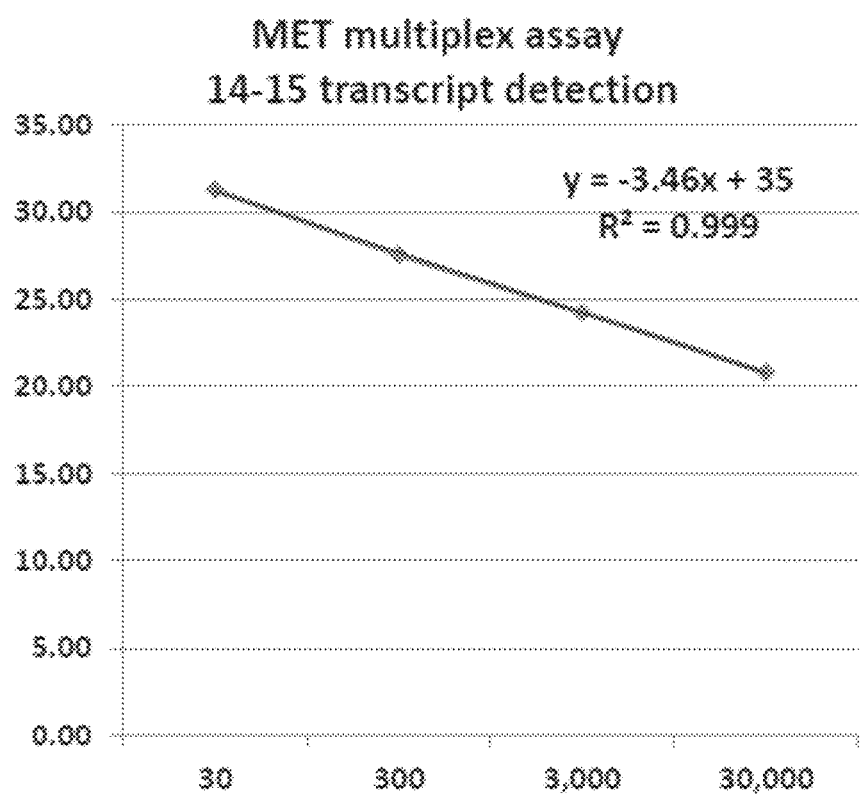
FIG. 6 shows the result of the multiplex for the wild type form exon 14-exon 15 junction (JA270 channel). Again, the data show that Ct is inversely related to wild type copy number, the reaction is linear, and sensitive enough to detect 30 copies.

Results are shown in FIGS. 4-6. FIG. 4 shows signal of MET exon 14 deleted sample vs. copy number of exon 14 deleted RNA. FIGS. 5 and 6 show signal of wild type MET (exon 13-exon 14 and exon 14-exon 15, respectively) vs copy number of wild type RNA. Each of the graphs show that the assay is sensitive enough to detect 30 copies of target RNA input.

Figure 7:
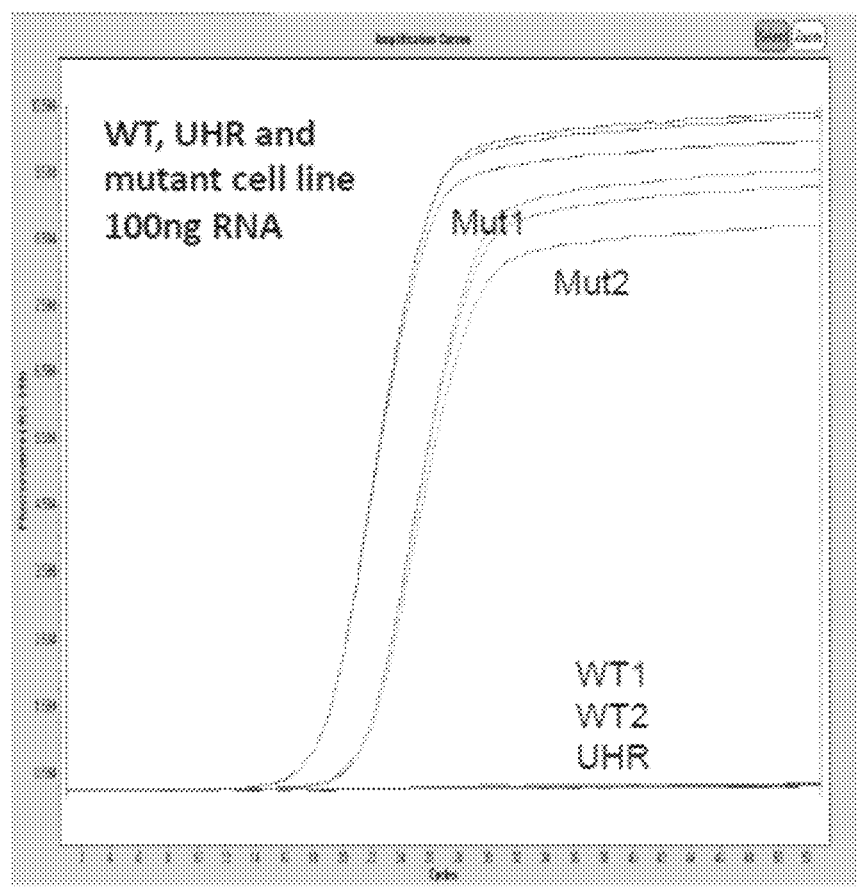
FIG. 7 shows that detection of the exon 13-exon 15 junction is specific. The x axis shows cycle number and the y axis shows FAM signal. Mut 1 and Mut2 are samples from MET exon 14 deleted cell lines. Wild type samples from WT1, WT2, and UHR (universal human RNA) do not generate a signal.

FIG. 7 shows that the assay is also specific. Signal of exon 13-exon 15 function (FAM) is shown for mutant cell lines (Mut 1 and Mut 2), wild type cell lines (WT1 and WT2), and universal human RNA (UHR). As shown in FIG. 7, no signal was detected for samples lacking the MET exon 14 deletion.

Figure 8:
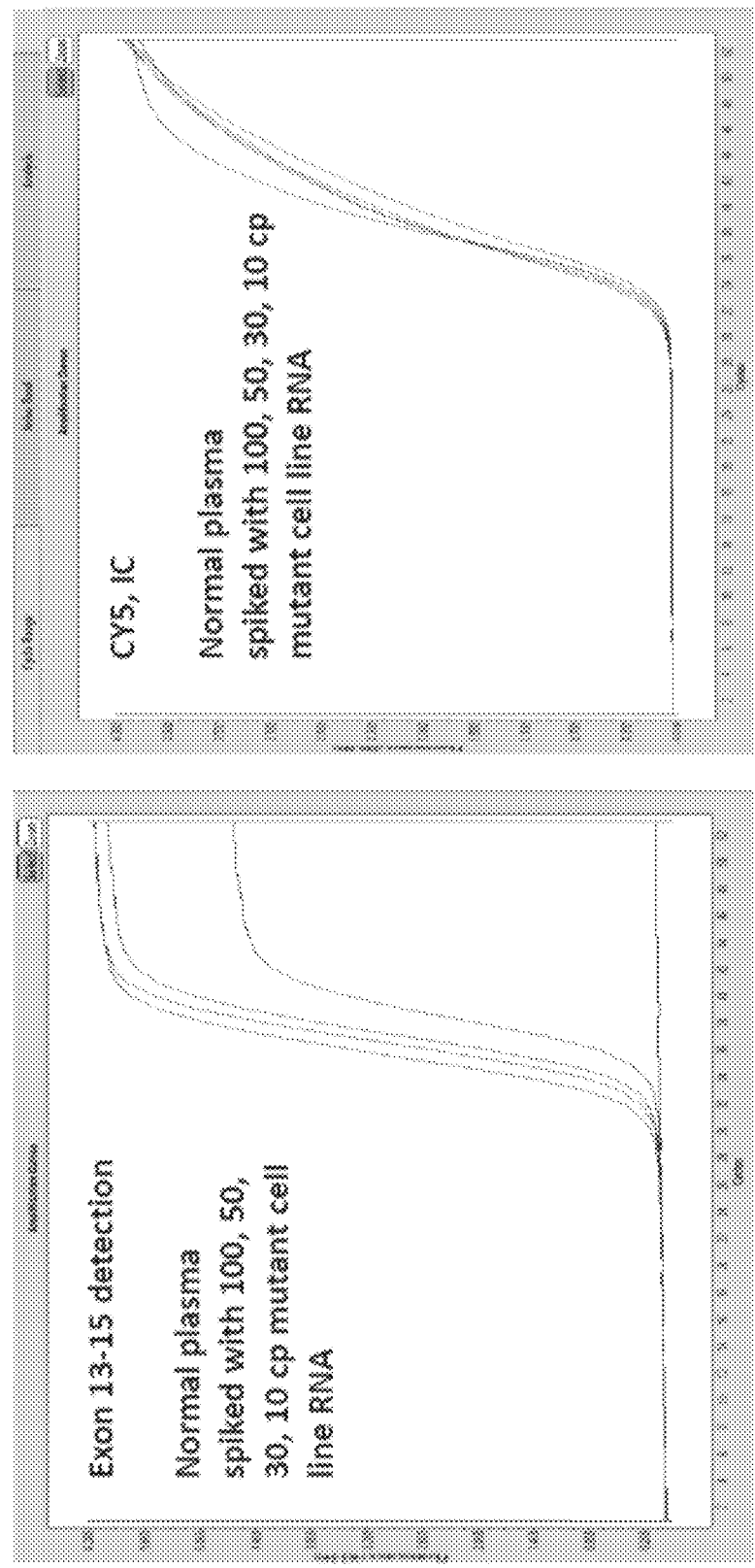
FIG. 8 shows the sensitivity of detection of the exon 13-exon 15 junction. Ct increases by about 2 between 100 copies and 30 copies mutant cell line RNA in wild type plasma, while a larger Ct increase is seen with only 10 copies mutant cell line RNA. The right panel shows the result of the internal control, which indicates roughly equal input between the samples.

C. MET Exon 14 Multiplex Reaction with Mutant Cell Line RNA Spiked Into Wild Type Plasma Nucleic acids from mutant cell lines was spiked into wild type (normal) plasma to ensure that plasma components (including wild type nucleic acids) would not interfere with detection of the mutant signal. As shown in FIG. 8, MET exon 14 deletion could be reliably detected in samples with 30 copies mutant RNA, with signal declining slightly with only 10 copies.

Figure 9:
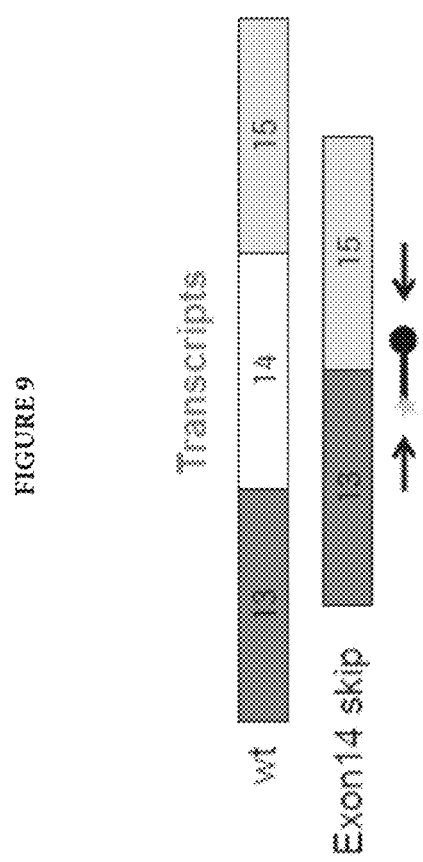
FIG. 9 shows an exemplary assay design. The top transcript represents unspliced wild type MET and the bottom transcript represents MET with exon 14 spliced out. The primer set (arrows) includes a first (forward) primer positioned in exon 13 and a second (reverse) primer positioned in exon 15 so that an amplification product is formed when exon 14 is spliced out. The probe is designed to specifically bind the amplification product, be it a sequence in exon 13 only, exon 15 only, or spanning an exon 13-exon 15 junction (as shown).

D. Assay Design (FIG. 9)

Using the assay design shown in FIGS. 2 and 3, exon 13-exon 13-exon 14 and exon 14-exon 15 amplification products are almost always produced regardless of whether the sample is MET wild type or has a MET exon 14 deletion. A different assay format was designed to focus on amplification and detection of the exon 13-exon 15 junction. In this case, only one MET amplification reaction is carried out, with a forward primer complementary to a sequence in exon 13 and a reverse primer complementary to a sequence in the opposite orientation in exon 15. The resulting amplification product has sequence from exon 13 and sequence from exon 15, and can be detected with a probe specific for any portion of the amplification product. That is, the probe can be specific for exon 13 sequence only, exon 15 sequence only, or junction of the exon sequences. MET splicing is heterogeneous, and thus multiple variant amplification products can be produced. The probe can be designed to capture multiple exon 14 splice variants, or multiple probes can be designed to capture different exon 14 splice variants.

E. Performance of MET Exon 13-exon 15 Amplification and Detection

Suitable MET13-FWD and MET15-REV primers, and MET13-15-PRB probes are shown in Table 1 above. An exception is the MET13-15-PRB9 antisense orientation probe that does not hybridize to MET exon 13-exon 15 amplification products, and that can be used for a control.

Figure 10:
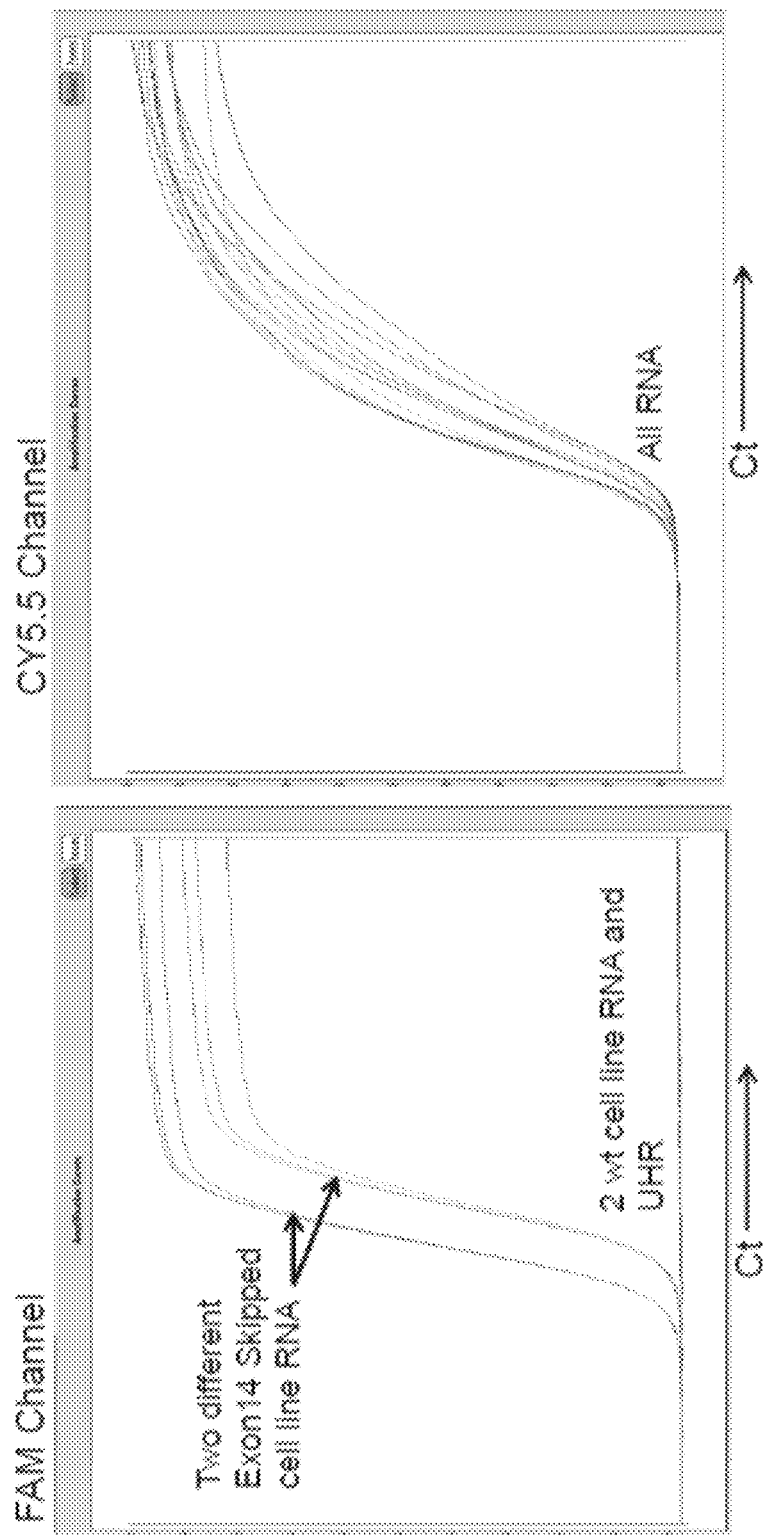
FIG. 10 shows the specifically of the assay design depicted in FIG. 9. The probe specific for the exon 13-exon 15 amplification product is labeled with FAM (left graph), while a probe specific for an internal control RNA is labeled with CY5.5 (right graph). qRT-PCR is shown for RNA from 2 cell lines with exon 14 spliced out (noted in left graph), 2 wild type cell lines, and UHR (Universal Human RNA).

FIG. 10 shows the specificity of the assay design depicted in FIG. 9. The probe specific for the exon 13-exon 15 amplification product is labeled with FAM (left graph), while a probe specific for an internal control RNA is labeled with CY5.5 (right graph). qRT-PCR is shown for RNA from 2 cell lines with exon 14 spliced out (noted in left graph), 2 wild type cell lines, and UHR (Universal Human RNA). Only the exon 14 spliced samples show signal.

Figure 11:
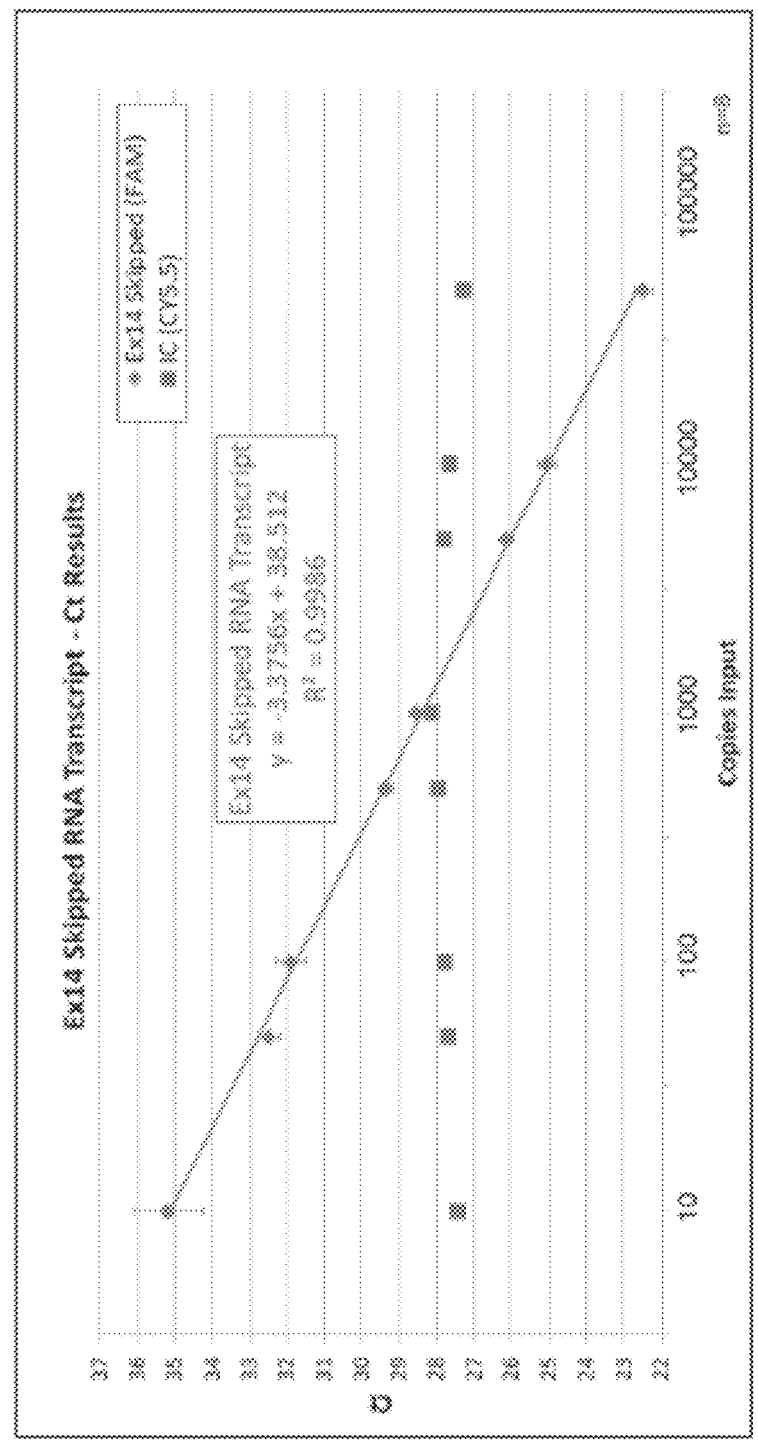
FIG. 11 shows Limit of Detection (LOD) and Linearity data using the amount the MET exon 14 spliced transcript indicated on the x-axis spike into 0.1 ng/reaction UHR. The splice product is detectable in the linear range down to 10 copies.

FIG. 11 shows Limit of Detection (LOD) and Linearity data using the amount of MET exon 14 spliced transcript indicated on the x-axis spliced into 0.1 ng/reaction UHR. The exon 14 spliced transcript is detectable in the linear range down to 10 copies. Internal control is indicated with squares and exon 14 spliced transcript is indicated with diamonds.

Figure 12:
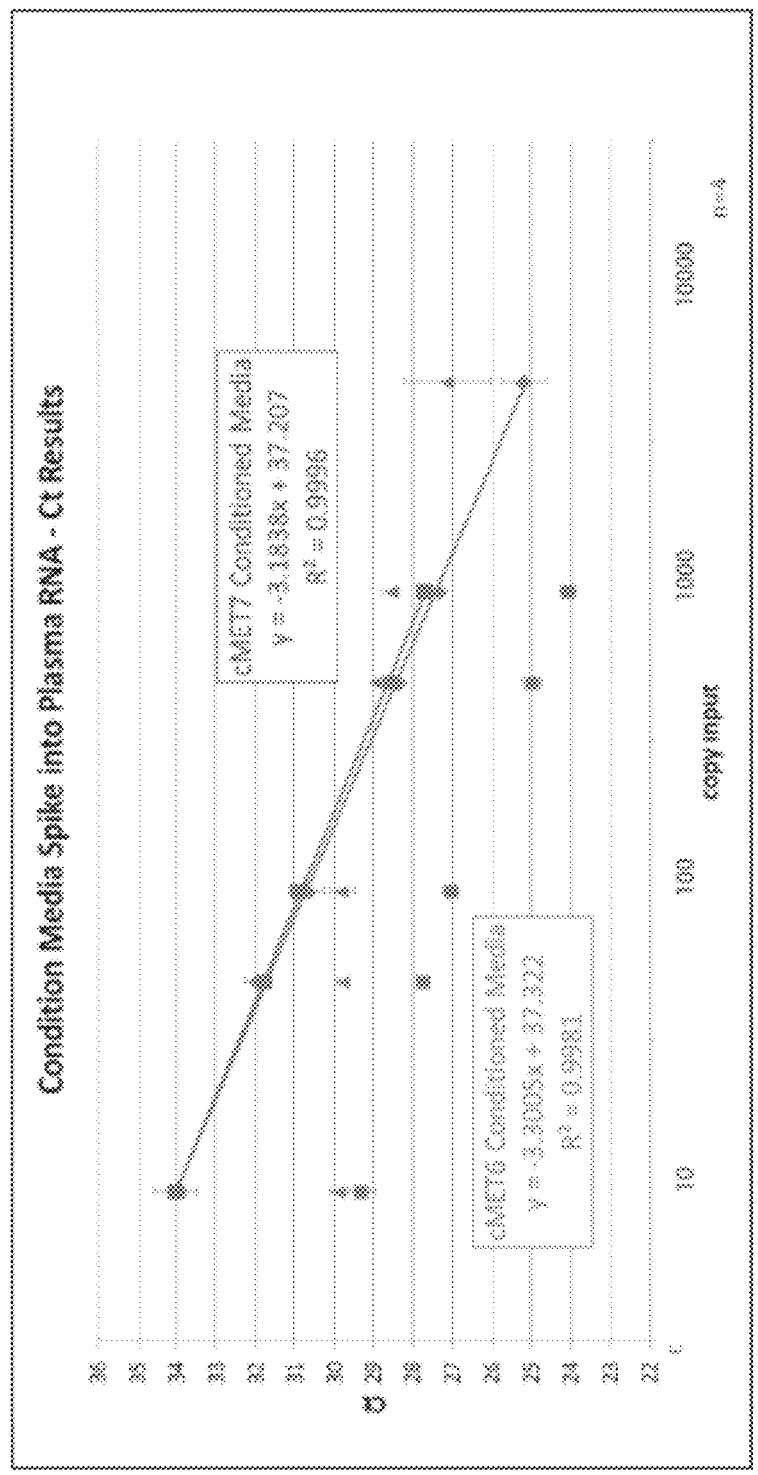
FIG. 12 shows LOD and Linearity using MET exon 14 spliced transcript from 2 different cell lines in the amount indicated on the x-axis spiked into 50 ng RNA from FFPET (formaldehyde fixed paraffin embedded tissue). The splice product is detectable in the linear range down to 10 copies.

FIG. 12 show LOD and Linearity using MET exon 14 spliced transcript from 2 different cell lines in the amount indicated on the x-axis spiked into 50 ng RNA from FFPET (formaldehyde fixed paraffin embedded tissue). The exon 14 spliced transcript is detectable in the linear range down to 10 copies. The exon 14 spliced cell line transcripts from cell lines are shown in squares and diamonds (along the line) with the internal controls in squares and triangles, respectively.

Figure 13:
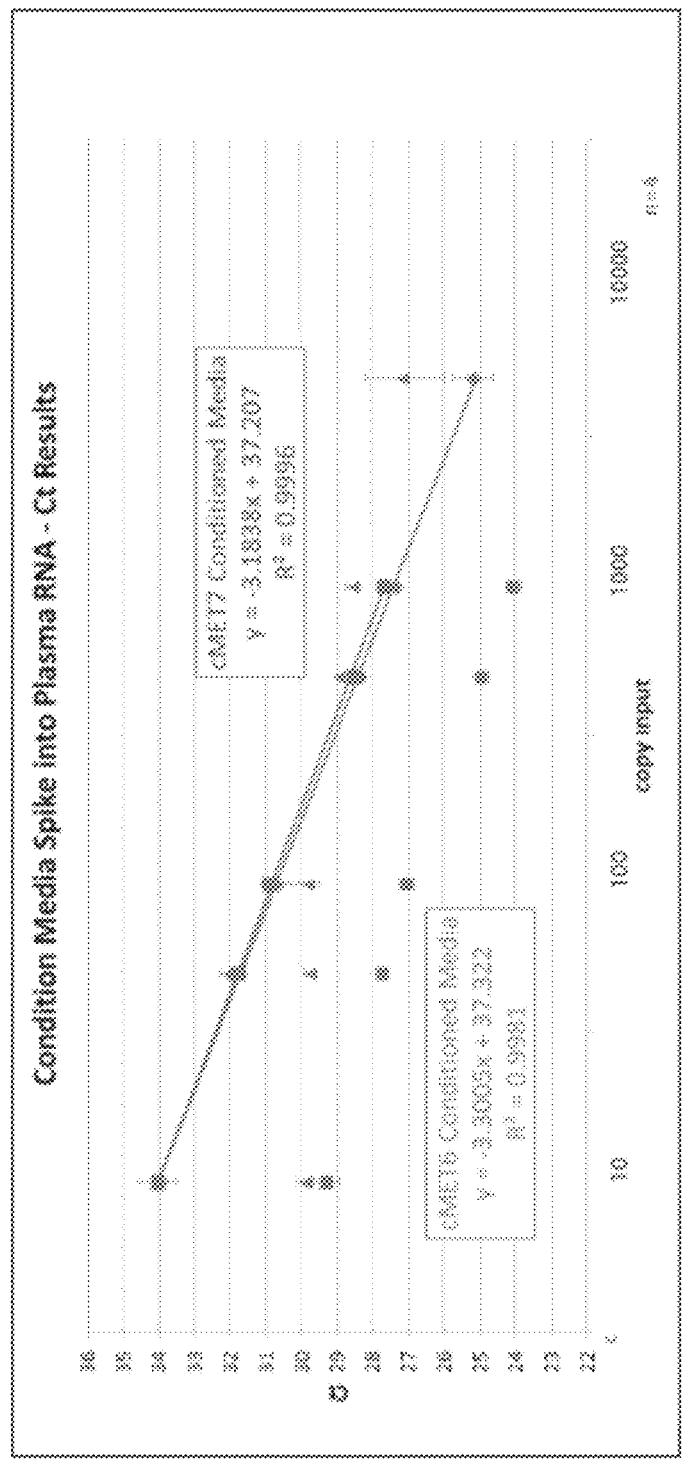
FIG. 13 shows LOD and Linearity data using MET exon 14 spliced transcript from 2 different cell lines in the amount indicated on the x-axis spiked into RNA from healthy donor plasma cfRNA. Again, the LOD is about 10 copies in the linear range.

FIG. 13 shows LOD and Linearity data using MET exon 14 spliced transcript from 2 different cell lines in the amount indicated on the x-axis spiked into RNA from healthy donor plasma cfRNA. Again, the LOD is about 10 copies in the linear range. The exon 14 spliced cell line transcripts from cell lines are shown in squares and diamonds (along the line) with the internal control in squares and triangles, respectively.

While the invention has been described in detail with reference to specific examples, it will be apparent to one skilled in the art that various modifications can be made within the scope of this invention. Thus the scope of the invention should not be limited by the examples described herein. All patents, publications, websites, Genbank (or other database) entries disclosed herein are incorporated by reference in their entireties.

---

We claim:

1. A method of providing treatment for an individual with cancer comprising:
   (a) obtaining a plasma or formalin fix paraffin embedded tissue (FFPET) sample comprising RNA from the individual;
   (b) carrying out a reverse transcription reaction on the RNA to produce cDNA;
   (c) carrying out an amplification reaction comprising contacting the cDNA with (i) a primer set and a first probe labeled with a first label that specifically amplify and detect MET exon 13-14 junction, (ii) a primer set and a second probe labeled with a second label that specifically amplify and detect MET exon 14-15 junction, and (iii) a primer set and a third probe labeled with a third label that specifically amplify and detect MET exon 13-15 junction;
   (d) detecting the presence of a MET exon 14 deletion if an amplification product is formed and detected by the primer set and the third probe of (iii); and
   (e) providing treatment for the individual with a MET inhibitor if a MET exon 14 deletion is present;
   wherein steps (b) and (c) are carried out in the same vessel, wherein the first probe is specific for the junction point of the MET exon 13-14 junction, the second probe is specific for the junction point of the MET exon 14-15 junction, and the third probe is specific for the junction point of the MET exon 13-15 junction, and wherein the third probe comprises a sequence selected from the group consisting of SEQ ID NOs: 53-55.

2. The method of claim 1, wherein step (c) further comprises contacting the cDNA with (iv) a primer set and a fourth probe labeled with a fourth label that specifically amplify and detect an internal control.

3. A method of detecting a MET exon 14 deletion comprising:
   (a) obtaining a plasma or formalin fixed paraffin embedded tissue (FFPET) sample comprising RNA from an individual;
   (b) carrying out a reverse transcription reaction on the RNA to produce cDNA;
   (c) carrying out an amplification reaction comprising contacting the cDNA with (i) a primer set and a first probe labeled with a first label that specifically amplify and detect MET exon 13-14 junction, (ii) a primer set and a second probe labeled with a second label that specifically amplify and detect MET exon 14-15 junction, and (iii) a primer set and a third probe labeled with a third label that specifically amplify and detect MET exon 13-15 junction; and
   (d) detecting the presence of a MET exon 14 deletion if an amplification product is formed and detected by the primer set and the third probe of (iii),
   wherein steps (b) and (c) are carried out in the same vessels, wherein the first probe is specific for the junction point of the MET exon 13-14 junction, the second probe is specific for the junction point of the MET exon 14-15 junction, and the third probe is specific for the junction point of the MET exon 13-15 junction, and wherein the third probe comprises a sequence selected from the group consisting of SEQ ID NOs: 53-55.

4. The method of claim 3, wherein step (c) further comprises contacting the cDNA with (iv) a primer set and a fourth probe labeled with a fourth label that specifically amplify and detect an internal control.

5. The method of claim 3, wherein the individual has cancer.

6. The method of claim 5, wherein the individual has non-small cell lung cancer (NSCLC).

7. The method of claim 5, further comprising providing treatment for the individual with a MET inhibitor if a MET 14 deletion is detected.

8. The method of claim 1, wherein the primer set for amplifying the MET exon 13-14 junction comprises a forward primer comprising a sequence selected from the group consisting of SEQ ID NOs: 1-8 and a reverse primer comprising a sequence selected from the group consisting of SEQ ID NOs: 17-24, and the first probe comprises a sequence selected from the group consisting of SEQ ID NOs: 44-46; wherein the primer set for amplifying the MET exon 14-15 junction comprises a forward primer comprising a sequence selected from the group consisting of SEQ ID NOs: 9-16 and a reverse primer comprising a sequence selected from the group consisting of SEQ ID NOs: 25-38, and the second probe comprises a sequence selected from the group consisting of SEQ ID NOs: 47-50; and wherein the primer set for amplifying the MET exon 13-15 junction comprises a forward primer comprising a sequence selected from the group consisting of SEQ ID NOs: 1-8 and reverse primer comprising a sequence selected from the group consisting of SEQ ID NOs: 25-38, and the third probe comprises a sequence selected from the group consisting of SEQ ID NOs: 53-55.

9. The method of claim 3, wherein the primer set for amplifying the MET exon 13-14 junction comprises a forward primer comprising a sequence selected from the group consisting of SEQ ID NOs: 1-8 and a reverse primer comprising a sequence selected from the group consisting of SEQ ID NOs: 17-24, and the first probe comprises a sequence selected from the group consisting of SEQ ID NOs: 44-46; wherein the primer set for amplifying the MET exon 14-15 junction comprises a forward primer comprising a sequence selected from the group consisting of SEQ ID NOs: 9-16 and a reverse primer comprising a sequence selected from the group consisting of SEQ ID NOs: 25-38, and the second probe comprises a sequence selected from the group consisting of SEQ ID NOs: 47-50; and wherein the primer set for amplifying the MET exon 13-15 junction comprises a forward primer comprising a sequence selected from the group consisting of SEQ ID NOs: 1-8 and reverse primer comprising a sequence selected from the group consisting of SEQ ID NOs: 25-38, and the third probe comprises a sequence selected from the group consisting of SEQ ID NOs: 53-55.

\* \* \* \* \*

SEQUENCE LISTING

```
<160> NUMBER OF SEQ ID NOS: 55

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ttgggttttt cctgtggct                                                 19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttgggttttt cctgtggct                                                 19
```

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 3
ttgggttttt cctgtggcu                                                 19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 4
ttgggttttt cctgtggcu                                                 19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
cttgggtttt tcctgtggct                                                20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
cttgggtttt tcctgtggct g                                              21

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
tgggtttttc ctgtggct                                                  18

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic

```
                            primer

<400> SEQUENCE: 8
ttgggttttt cctgtggctg                                              20

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcaaatgaat ctgtagacta ccg                                          23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcaaatgaat ctgtagacta ccg                                          23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcaaatgaat ctgtagacta ccg                                          23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcaaatgaat ctgtagacta ccg                                          23

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aatggtttca aatgaatctg tagact                                       26

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 14
aaatggtttc aaatgaatct gtagact                                              27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agaaatggtt tcaaatgaat ctgtaga                                              27

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaaatggttt caaatgaatc tgtagac                                              27

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gagtgtgtac tcttgcatcg ta                                                   22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 18
gagtgtgtac tcttgcatcg ua                                                   22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gagtgtgtac tcttgcatcg ta                                                   22

<210> SEQ ID NO 20
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 20
gagtgtgtac tcttgcatcg ua                                              22

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agtgtgtact cttgcatcgt                                                 20

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gagtgtgtac tcttgcatcg ta                                              22

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgaggagtgt gtactcttgc a                                               21

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gaggagtgtg tactcttgca                                                 20

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgcacttgtc ggcatgaa                                                   18

<210> SEQ ID NO 26
<211> LENGTH: 19
<212> TYPE: DNA
```

-continued

<213> ORGANISM: Artificial Sequence
<220> FEATURE:
<223> OTHER INFORMATION: Description of Artificial Sequence: Synthetic
      primer

<400> SEQUENCE: 26
ctgcacttgt cggcatgaa                                                   19

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 27
ctgcacttgt cggcaugaa                                                   19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 28
ctgcacttgt cggcaugaa                                                   19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cttgtcggca tgaaccgtt                                                   19

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ttgtcggcat gaaccgtt                                                    18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cttgtcggca tgaaccgt                                                    18

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
acttgtcggc atgaaccgt                                              19

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
tgcacttgtc ggcatgaac                                              19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
ctgcacttgt cggcatgaa                                              19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
gcacttgtcg gcatgaacc                                              19

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
ctgcacttgt cggcatgaac                                             20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
ttgtcggcat gaaccgttct                                             20

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtcggcatga accgttct                                                  18

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
agaaagcaaa ttaaagatca gtttcctaat tcat                                34

<210> SEQ ID NO 40
<211> LENGTH: 34
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 40
agaaagcaaa ttaaagauca gtttcctaat tcat                                34

<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 41
agaaagcaaa ttaaagauca gtttcctaat tcat                                34

<210> SEQ ID NO 42
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
agaaagcaaa ttaaagatca gtttcctaat tcat                                34

<210> SEQ ID NO 43
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

```
<220> FEATURE:
<223> OTHER INFORMATION: Description of Combined DNA/RNA Molecule:
      Synthetic probe

<400> SEQUENCE: 43
agaaagcaaa ttaaagauca gtttcctaat tcat                              34

<210> SEQ ID NO 44
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
agaaagcaaa ttaaagatct gggcagtgaa ttag                              34

<210> SEQ ID NO 45
<211> LENGTH: 34
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 45
agaaagcaaa ttaaagauct gggcagtgaa ttag                              34

<210> SEQ ID NO 46
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
agaaagcaaa ttaaagatct gggcagtgaa ttag                              34

<210> SEQ ID NO 47
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
agctactttt ccagaagatc agtttcctaa ttcat                             35

<210> SEQ ID NO 48
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
agctactttt ccagaagatc agtttcctaa ttcat                             35

<210> SEQ ID NO 49
<211> LENGTH: 35
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
agctactttt ccagaagatc agtttcctaa ttcat                              35

<210> SEQ ID NO 50
<211> LENGTH: 35
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 50
agctactttt ccagaagauc agtttcctaa ttcat                              35

<210> SEQ ID NO 51
<211> LENGTH: 34
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 51
agaaagcaaa ttaaagauca gtttcctaat tcat                               34

<210> SEQ ID NO 52
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
agcaaattaa agatcagttt cctaattcat ctcag                              35

<210> SEQ ID NO 53
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
ttaaagatca gtttcctaat tcatctcaga acgg                               34

<210> SEQ ID NO 54
<211> LENGTH: 34
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
```

```
<400> SEQUENCE: 54
tuaaagatca gtttcctaat tcatctcaga acgg                              34

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
aatttctagt caaaggatta agtagagtct tgcc                              34
```